(12) United States Patent
Chu

(10) Patent No.: US 9,155,603 B2
(45) Date of Patent: Oct. 13, 2015

(54) MEDICAL DEVICE FOR DELIVERY OF BODILY IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 189 days.

(21) Appl. No.: 13/610,302

(22) Filed: Sep. 11, 2012

(65) Prior Publication Data
US 2013/0079591 A1  Mar. 28, 2013

Related U.S. Application Data

(60) Provisional application No. 61/538,463, filed on Sep. 23, 2011.

(51) Int. Cl.
| | |
|---|---|
| A61F 2/00 | (2006.01) |
| A61F 13/00 | (2006.01) |
| A61B 17/04 | (2006.01) |
| A61B 17/06 | (2006.01) |
| A61B 17/00 | (2006.01) |

(52) U.S. Cl.
CPC .......... *A61F 2/0045* (2013.01); *A61B 17/0482* (2013.01); *A61B 17/0483* (2013.01); *A61B 17/06109* (2013.01); *A61B 2017/00805* (2013.01); *A61B 2017/06009* (2013.01); *A61B 2017/06042* (2013.01)

(58) Field of Classification Search
CPC ................... A61F 2/0045; A61B 2017/00805; A61B 17/0482; A61B 2017/06042; A61B 17/06109; A61B 2017/06009; A61B 17/0483
USPC ........................ 600/37, 29–31; 128/897–899
See application file for complete search history.

(56) References Cited

U.S. PATENT DOCUMENTS

| | | | |
|---|---|---|---|
| 5,385,561 A | 1/1995 | Cerny | |
| 5,782,862 A | 7/1998 | Bonutti | |
| 8,777,837 B2 * | 7/2014 | Ogdahl et al. | 600/37 |
| 2003/0009181 A1 * | 1/2003 | Gellman et al. | 606/151 |

(Continued)

FOREIGN PATENT DOCUMENTS

| | | |
|---|---|---|
| WO | 98/46142 A1 | 10/1998 |
| WO | 2009/038781 A1 | 3/2009 |
| WO | 2013043432 A1 | 3/2013 |

OTHER PUBLICATIONS

Search Report and Written Opinion for PCT Application No. PCT/US2012/05854, mailed Nov. 20, 2012, 21 pages.

(Continued)

*Primary Examiner* — Christine H Matthews
*Assistant Examiner* — Sunita Reddy
(74) *Attorney, Agent, or Firm* — Brake Hughes Bellermann LLP

(57) ABSTRACT

A medical device and a method for delivering a bodily implant are disclosed. The medical device includes an insertion member, an adjustment member and a button. The insertion member further includes a tip. The insertion member has a curved portion proximate the tip and a straight portion distally located from the tip. The curved and straight portions are configured to be placed into a channel within a housing of the insertion member. The adjustment member is coupled to the insertion member distally and is configured to be advanced and retracted, thereby advancing and retracting the insertion member with respect to the housing. The button is moveable coupled to the housing of the insertion member.

17 Claims, 23 Drawing Sheets

(56) References Cited

U.S. PATENT DOCUMENTS

| | | |
|---|---|---|
| 2004/0087970 A1 | 5/2004 | Chu et al. |
| 2004/0162569 A1* | 8/2004 | Sikora et al. .................. 606/148 |
| 2008/0103527 A1 | 5/2008 | Martin et al. |
| 2009/0216250 A1 | 8/2009 | Zipper |
| 2010/0094363 A1* | 4/2010 | Martinek et al. ............ 606/86 R |
| 2011/0015675 A1* | 1/2011 | Howard et al. ............... 606/232 |

OTHER PUBLICATIONS

International Preliminary Report on Patentability for PCT Application No. PCT/US2012/05854, mailed Apr. 3, 2014, 10 pages.

* cited by examiner

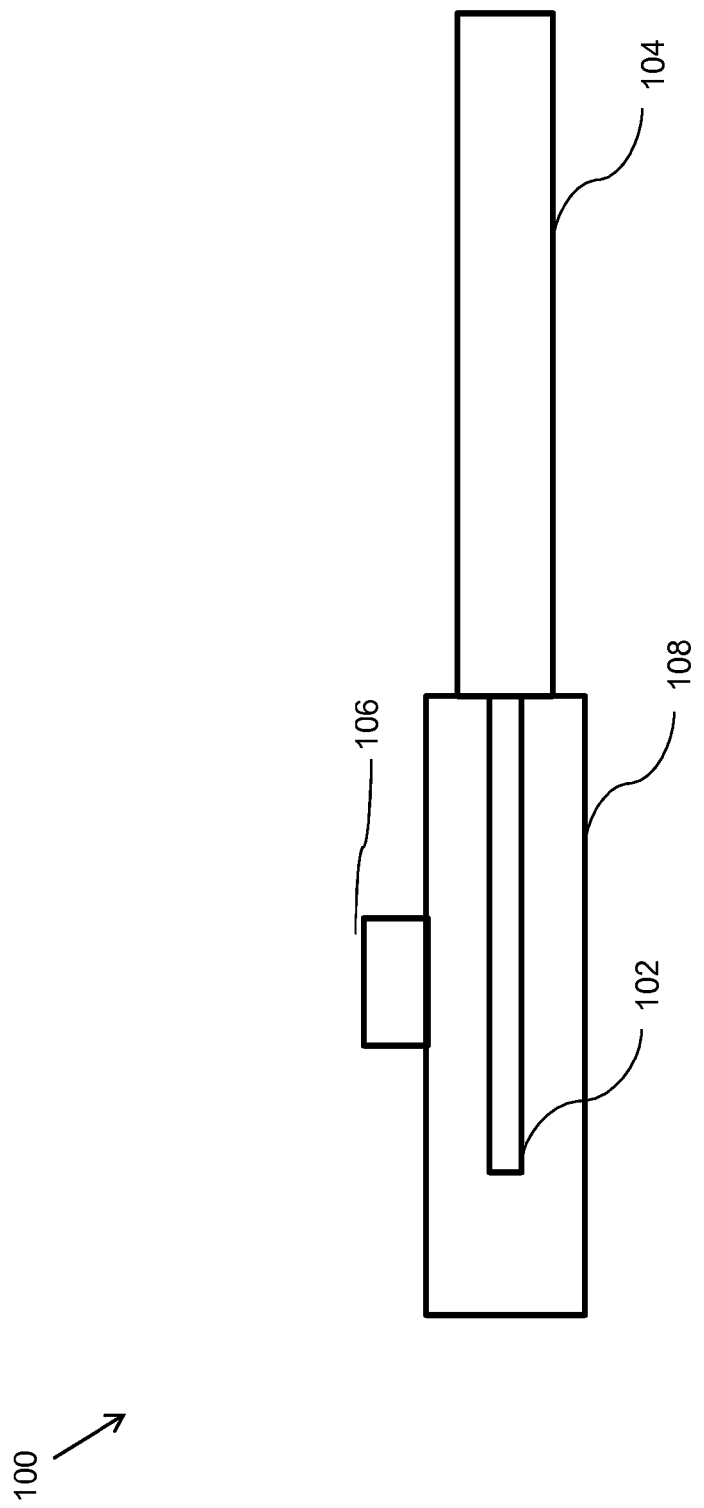

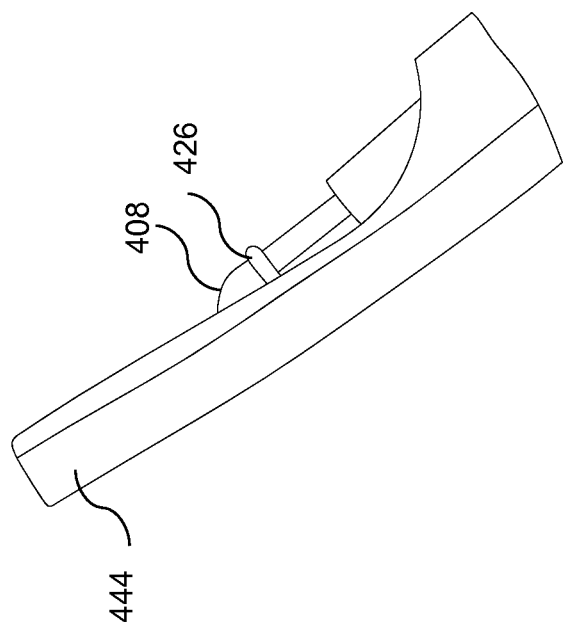

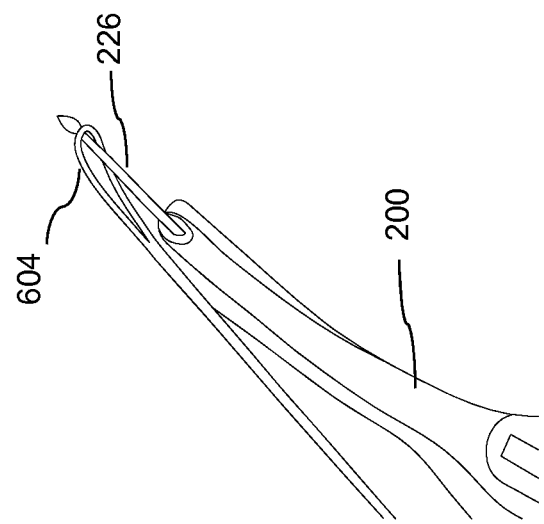

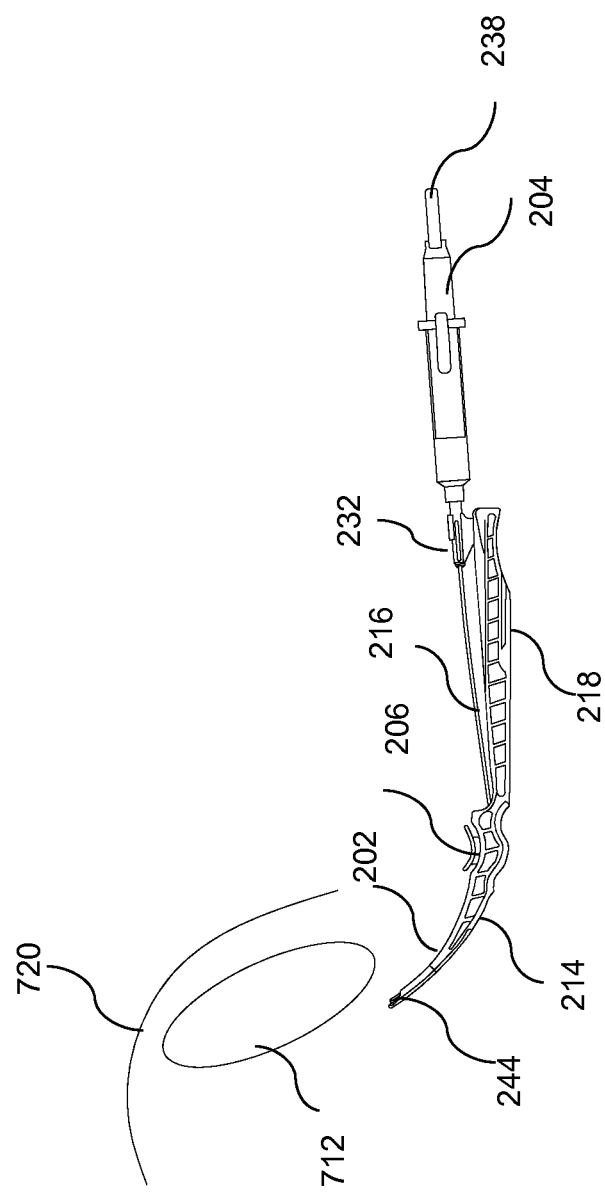

MEDICAL DEVICE FOR DELIVERY OF BODILY IMPLANTS

CROSS-REFERENCE TO RELATED APPLICATION

This application is a Nonprovisional of, and claims priority to, U.S. Patent Application No. 61/538,463, filed Sep. 23, 2011, entitled "MEDICAL DEVICE FOR DELIVERY OF BODILY IMPLANTS", which is incorporated by reference herein in its entirety.

BACKGROUND

1. Field

The present invention generally relates to a medical device and surgical procedures, and particularly medical devices and methods used for delivering a bodily implant in a patient's body for the treatment of a pelvic floor disorder.

2. Description of the Related Art

Urinary incontinence is defined as the involuntary leakage of urine. While, primarily this is a problem seen in women, men also suffer from urinary incontinence. There are many reasons that can cause urinary incontinence such as loss of bladder control. Among women, the problem may be associated with a specific condition called Stress Urinary Incontinence. Stress urinary incontinence is the involuntary loss of urine during physical activity such as coughing, laughing, or lifting. The muscles that support the urethra and bladder neck get weakened, causing the urethra to drop during physical activity, resulting in urine leaking out of the body.

Various techniques for performing implant-based surgical procedures have evolved over the last years. The implants may be delivered inside the patient's body using a delivery device that acts as a carrier and facilitate in delivery and placement of the implant. Several types of such delivery devices and methods exist that assist in delivery of the implant inside a patient's body such as a needle assembly having a long curved needle tip. The long curved needles may deflect easily and may be difficult to direct and control. Misdirected needles can cause injury to the bladder, urethra and bowel, thereby increasing complexity in the procedures of delivery and placement of the implant.

Accordingly there exists a need for a delivery device that satisfactorily delivers the implants. Further, a need exists for methods for delivering the implant with a delivery device that minimizes discomfort and recovery time.

SUMMARY

A medical device and a method for delivering a bodily implant in a patient's body are disclosed. The medical device includes an insertion member, an adjustment member and a button. The insertion member further includes a tip. The insertion member has a curved portion proximate the tip of the insertion member and a straight portion distally located from the tip. The curved and straight portions of the insertion member are configured to be placed into a channel within a housing of the insertion member. The adjustment member is coupled to the insertion member distally and is configured to be advanced and retracted, and thereby advancing and retracting the insertion member with respect to the housing. The button is moveably coupled to the housing of the insertion member. The button is configured to elevate away from a surface of the housing as the insertion member advances with respect to the housing and is configured to be lowered toward the housing by an application of force and contact the insertion member so as to deflect and friction fit it within the channel. The button is further configured to temporarily fix location of the insertion member with respect to the housing.

BRIEF DESCRIPTION OF THE FIGURES

The invention and the following detailed description of certain embodiments thereof may be understood with reference to the following figures:

FIG. 1 is a schematic diagram of a medical device configured to deliver a bodily implant in a patient's body, in accordance with an embodiment of the present invention.

FIG. 4B illustrates an enlarged view of a portion of the medical device of FIG. 4A, in accordance with an embodiment of the present invention.

FIG. 6B is an enlarged view of an association of an implant with the medical device, in accordance with an embodiment of the present invention.

FIGS. 7A-7E illustrate method of use of a medical device for placement of an implant in a patient's body, in accordance with an embodiment of the present invention.

DETAILED DESCRIPTION

Figure 2A:
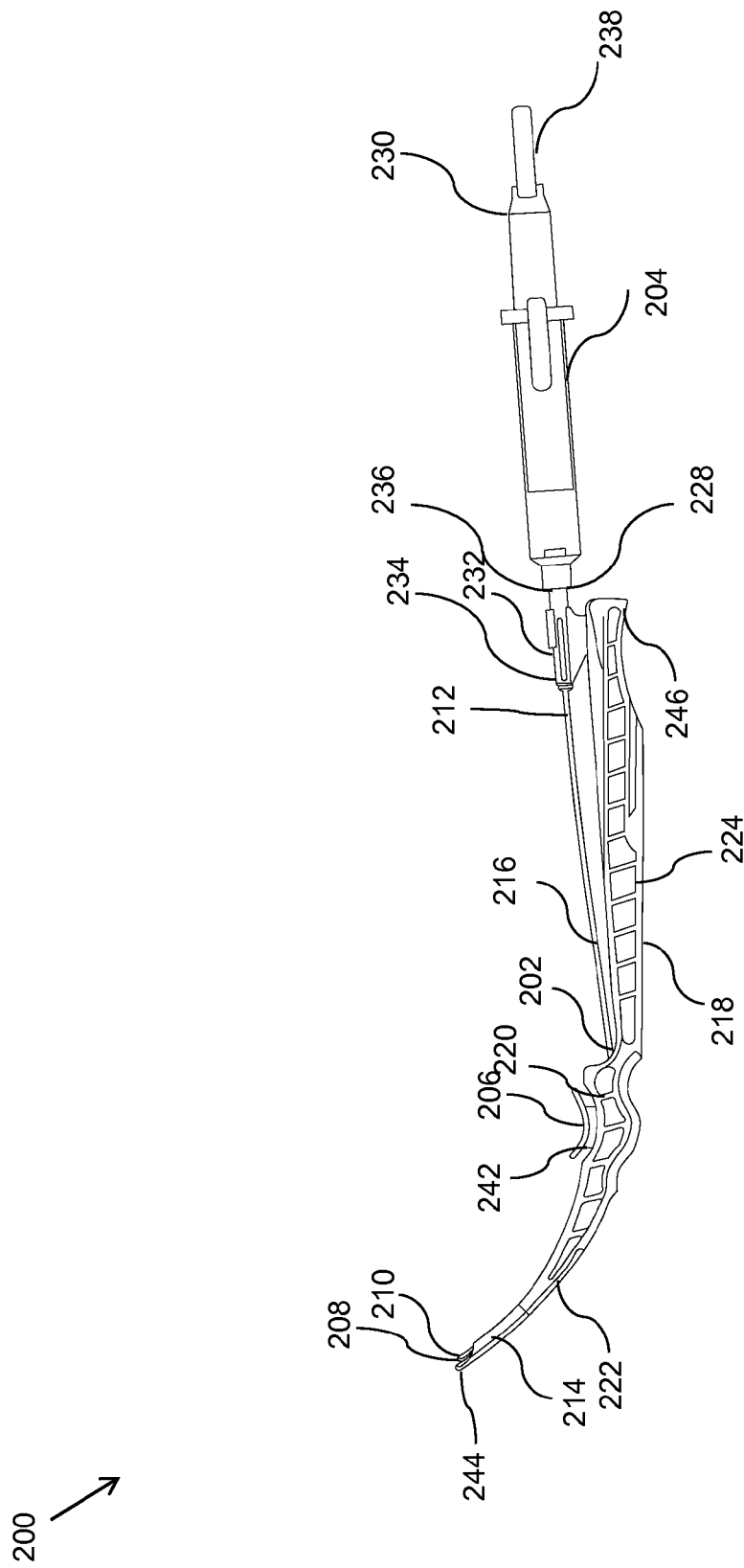
FIG. 2A illustrates a side view of a medical device configured to deliver a bodily implant in a patient's body, in accordance with an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The term patient may hereafter be used for a person who benefits from the medical device or the methods disclosed in the present invention. For example, the patient can be a person whose body is operated through the medical device or the method disclosed by the present invention. In various embodiments, the patient may be a human female, a human male, or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

FIG. 1 is a schematic diagram of a medical device 100 configured to deliver a bodily implant (not shown) in a patient's body. The bodily implant can be a mesh-based device, such as a sling, and the like, used in the treatment of fecal incontinence, urinary incontinence, prolapse, and other such disorders. The medical device 100 includes an insertion member 102, an adjustment member 104, and a button 106.

The insertion member 102 includes a tip and is configured to be inserted into a tissue layer and/or puncture bodily tissues. In some embodiments the tip may be blunt. In other embodiments the tip may be sharp. In certain embodiments the tip may be conical in shape. In other embodiments the tip may have any other shape. The insertion member 102 further includes a proximal end portion and a distal end portion.

The insertion member 102 can have a variety of shapes and sizes depending on the surgical requirements. In certain embodiments, the insertion member 102 can be a surgical needle configured to pierce through the patient's body during insertion. The surgical needle may be made of a metal such as stainless steel.

The insertion member 102 has a curved portion proximate the tip of the insertion member 102 and a straight portion distally located from the tip of the insertion member 102. The insertion member 102 is configured to be disposed within an insertion member 102 housing 108. The insertion member housing 108 may hereafter be referred to as housing 108 merely for the purpose of simplicity of the description without limiting the scope of the invention. The hosing 108 includes a channel or a passageway such that a portion of the insertion member 102 or the complete insertion member 102 is configured to move within the insertion member channel. The channel includes a curved portion and a straight portion. In some embodiments, the curved and straight channel portions are designed with curvatures that are substantially similar to the curvatures of the curved and straight portions of the insertion member 102. For example, the curvature of the curved portion of the channel can be similar to the curvature of the curved portion of the insertion member 102 such that upon disposing the insertion member 102 within the channel, the curved portion of the insertion member 102 can easily sit into the curved portion of the channel without being deflected or stressed due to flexing, bending or deflection. Similarly, the curvature of the straight portion of the channel can be similar to the curvature of the straight portion of the insertion member 102 such that the straight portion of the insertion member 102 can sit into the straight portion of the channel without being deflected or stressed due to flexing, bending or deflection. Therefore, the complete insertion member 102 is configured to be disposed and sit inside the channel without being stressed due to the bending or deflection in at least one of the configurations. The configurations may be defined as a location of the insertion member 102 with respect to the housing 108 or the insertion member channel. There can be innumerable configurations based on the various locations of the insertion member 102 with respect to the housing 108 of the insertion member channel.

The above discussion exemplifies a specific embodiment that utilizes a curved portion and a straight portion of the insertion member 102. In certain other embodiments, the straight portion may be replaced by a curved portion that is not substantially straight such that a first curved portion and a second curved portion are provided in the insertion member 102. In accordance with this embodiment, the first curved portion and the second curved portion have a substantial difference in the degree of curvatures of the first curved portion and the second curved portion. Similarly, the channel may also have a first curved portion and a second curved portion such that there is a substantial difference between the degree of curvatures of the first curved portion and the second curved portion of the channel. In accordance with this embodiment, the complete insertion member 102 is still configured to be disposed and sit inside the channel without being stressed due to the bending or deflection in at least one of the configurations. The at least one of the configurations may be a completely retracted configuration in which the complete channel is covered by the insertion member 102 or a portion of the insertion member 102. The completely retracted configuration is further described later.

In some other embodiments, the insertion member 102 may be substantially flexible and configured to assume a shape according shape of the insertion member channel. In accordance with these embodiments, the curvatures of the insertion member 102 may not be similar to the curvatures of the insertion member channel. However, since the insertion member 102 is flexible, it is configured to convert its shape into the shape that is similar to the insertion member channel upon deflection. For example, the shape of the insertion member 102 may change as the insertion member 102 is extended inside the channel. This causes the insertion member 202 to be spring loaded upon deflection. Also, the deflected portion may tend to straighten itself out to regain its original shape causing it to be spring loaded further.

In some embodiments, the insertion member 102 can include a lumen that extends from the proximal end portion to the distal end portion of the insertion member 102. In some embodiments, the insertion member 102 has a small outer diameter to minimize injury to patients. For example, in some embodiments, the outer diameter may be 0.062 inches. In other embodiments, the dimensions of the outer diameters may be different.

In certain embodiments, the insertion member 102 can be a surgical needle configured to pierce through the patient's body during insertion and then manipulate through the bodily tissues. The surgical needle may be made of a metal such as a stainless steel.

In some embodiments, the insertion member 102 may have a slot for association to an implant or to an association loop (for example a suture or a thread) of the implant. In an embodiment, the slot can be provided at the tip of the insertion member 102. In accordance with some embodiments, the slot is at least one selected from the group consisting of a T slot, an L slot, an angle shaped slot, and the like. The T slot can be configured to prevent the association loop from coming out of the slot for example during bi-directional manipulation of the insertion member 102 during placement. In some embodiments, the insertion member 102 may be associated to a carrier or a dart or an anchor of the implant at the tip of the insertion member 102.

In some embodiments, the channel of the insertion member 102 that is provided within the housing 108 can have various dimensions based on requirements and based on dimensions of the insertion member 102 that is configured to be disposed within the channel. In some embodiments, the width of the channel is slightly more than the outer diameter of the insertion member 102. Further, in some other embodiments, the width of the channel can be substantially greater than the diameter of the insertion member 102. Further, in some embodiments, the height of the channel is slightly more than the outer diameter of the insertion member 102. In some other embodiments, the height of the channel can be substantially greater than the diameter of the insertion member 102. The insertion member 102 can also have varying heights.

The medical device further includes the adjustment member 104 as discussed above. The adjustment member 104 is configured to be coupled to the insertion member 102 distally and configured to be advanced and retracted, thereby advancing and retracting the insertion member 102 with respect to the housing 108 or the insertion member channel. The adjustment member 104 has a proximal end portion and a distal end portion.

In some embodiments, the adjustment member 104 includes a hub coupled to the distal end portion of the insertion member 102 and configured to be advanced and retracted based on an application of an external force. The straight portion of the insertion member 102 may terminate at the hub. The hub has a proximal end portion and a distal end portion. The proximal end portion of the hub may be configured to be coupled to the insertion member 102 through various coupling mechanisms such as a luer connection.

In some other embodiments, the adjustment member 104 includes a hub and a syringe. The hub is similar to that described above and having a proximal end portion and a distal end portion similar to the hub described above. The syringe is configured to be coupled to the distal end of the hub. In certain embodiments, the lumen of the insertion member 102 may be used to deliver medications such as anesthetics and the like through the syringe. In other embodiments the syringe can also be used as a handle. In some embodiments, a three ring syringe is used. In other embodiments, a two ring syringe or an O-ring and the like kinds of syringes may be used. In some embodiments, the syringe may be connected to the hub through a medical luer connection. In other embodiments, the syringe may be connected to the hub through other kinds of connections and coupling or fasteners. In some embodiments, the syringe can be removably coupled to the hub. In other embodiments, the syringe can be fixedly coupled to the hub such that the hub and the syringe form an integral part of the adjustment member 104.

In some embodiments, the proximal end of the hub is configured to be coupled to the insertion member 102 such that the insertion member 102 is configured to be advanced and/or retracted based on an application of an external force and/or release of the force exerted through the syringe. In other embodiments, the hub can be advanced and/or retracted based on an application of an external force and/or release of the force exerted through the hub directly, when the syringe is not used.

In some embodiments, the adjustment member 104 can further include an orientation indicator. The orientation indicator may be configured to indicate a degree of orientation of the insertion member tip while the insertion member 102 advances into a bodily tissue. In some embodiments, the orientation indicator includes wings or ears that are positioned along the distal portion of the adjustment member 104 circumferentially. The orientation indicator may provide a visual indication of the tip orientation of the housing and/or insertion member 102 such that it relates to row, yaw and pitch movements of the medical device 100.

In some embodiments, the housing of the insertion member 102 is inserted inside the body. The insertion member 102 is then advanced with respect to the housing to a defined depth inside the body till the tip of the insertion member contacts pubic bone. As soon as the contact with the pubic bone is felt, the insertion member 102 is rotated along an X-X axis (as shown in FIG. 7E later as a dot) that extends orthogonally through the page containing the figure. The angle of rotation of the insertion member 102 can be felt as well as seen by the orientation indicator as described above. In this manner, the insertion member 102 is further capable of being advanced past the pubic bone after it is rotated.

As discussed above, the medical device 100 further includes the button 106. The button 106 can be moveably coupled to the housing 108 of the insertion member 102. In various embodiments, the button 106 may be coupled to the housing 108 of the insertion member 102 through various fasteners that provide the capability to the button to move with respect to the housing. For example, in some embodiments, the button may include projections on one or multiple sides such that these projections are configured to slide through one or multiple recesses provided in the housing 108. In accordance with various other embodiments, various other sliding mechanisms can be provided to cause the button to move with respect to the housing 108.

The button 106 is configured to elevate away from a surface of the housing 108 as the insertion member 102 advances through the insertion member channel. The button 106 is further configured to be lowered toward the housing 108 by an application of force and contact the insertion member 102 so as to deflect and friction fit it within the insertion member channel 220 against inner surface of the channel 220. The button 106 is further configured to temporarily fix location or position of the insertion member 102 with respect to the housing or the insertion member channel. The housing 108 may further include a button channel such that the button 106 is configured to move inside the button channel up and down with respect to the insertion member channel. Further, the insertion member 102 when disposed inside the housing 108 is configured to extend through the button channel. In accordance with some embodiments, the button 106 is at least one selected from the group consisting of a lever, a trigger and the like.

The insertion member channel includes the curved portion and the straight portion as discussed above. In a completely advanced or extended position of the insertion member 102 with respect to the housing 108, the straight portion of the insertion member 102 may be configured to fit into the curved portion of the housing 108 upon advancement with the use of the adjustment member 104. This may cause the button 106 to elevate away from the housing 108. In a completely retracted position of the insertion member 102 with respect to the housing 108, the straight portion of the insertion member 102 exits the curved portion of the housing 108 upon recede through the adjustment member 104. This may cause the button 106 to depress. In some embodiments, a resilient material-based element such as a spring, buffer, and the like may be provided that may be configured to actuate the button 106 and force the button 106 to move up and down with respect to the insertion member channel.

In accordance with some embodiments, the medical device 100 may not include the button 106, and the insertion member 102 can be fixed temporarily with respect to the housing by a user by gripping the insertion member 102.

FIG. 2A illustrates a perspective side view of a medical device 200, in accordance with an embodiment of the present invention. The medical device 200 includes an insertion member 202, an adjustment member 204, and a button 206.

The insertion member 202 includes a tip 208 and is configured to be inserted into a tissue layer and/or puncture bodily tissues. In some embodiments the tip 208 may be blunt. In other embodiments the tip 208 may be sharp. In certain embodiments the tip 208 may be conical in shape. In other embodiments the tip 208 may have any other shape. The insertion member 202 has a proximal end portion 210 and a distal end portion 212.

The insertion member 202 can have a variety of shapes and sizes depending on the surgical requirements. In certain embodiments, the insertion member 202 can be a surgical needle configured to pierce through a patient's body during insertion. The surgical needle may be made of a metal such as stainless steel.

The insertion member 202 has a curved portion 214 proximate the tip 208 of the insertion member 202 and a straight portion 216 distally located from the tip 208 of the insertion member 202. The insertion member 202 is configured to be disposed within an insertion member housing 218. The insertion member housing 218 may hereafter be referred to as housing 218 merely for the purpose of simplicity of the description without limiting the scope of the invention. The housing 218 includes a channel or a passageway 220 such that a portion of the insertion member 202 or the complete insertion member 202 is configured to move within the insertion member channel 220. The insertion member channel 220 includes a curved portion 222 and a straight portion 224. In some embodiments, the curved channel portion 222 and straight channel portion 224 are designed with curvatures that are substantially similar to the curvatures of the curved portion 214 and straight portion 216 of the insertion member 202. For example, the curvature of the curved portion 222 of the insertion member channel 220 can be similar to the curvature of the curved portion 214 of the insertion member 202 such that upon disposing the insertion member 202 within the channel 220, the curved portion 214 of the insertion member 202 can easily sit into the curved portion 222 of the channel 220 without being deflected or stressed due to flexing, bending or deflection. Similarly, the curvature of the straight portion 224 of the channel 220 can be similar to the curvature of the straight portion 216 of the insertion member 202 such that the straight portion 216 of the insertion member 202 can easily sit into the straight portion 224 of the channel 220 without being deflected or stressed due to flexing, bending or deflection. Therefore, the complete insertion member 202 is configured to be disposed and sit inside the channel 220 without being stressed due to the bending or deflection in at least one of the configurations. The configurations may be defined as a location of the insertion member 202 with respect to the housing 218 or the insertion member channel 220.

There can be innumerable configurations based on the various locations of the insertion member 202 with respect to the housing 218 or the insertion member channel 220.

In some embodiments, the insertion member 202 can include a lumen that extends from the proximal end portion to the distal end portion of the insertion member 202. In some embodiments, the insertion member 202 has a small outer diameter to minimize injury to patients. For example, in some embodiments, the outer diameter may be 0.062 inches. In other embodiments, the dimensions of the outer diameters may be different.

As illustrated, in some embodiments, the insertion member 202 may have a slot 226 (illustrated in FIG. 2B) for association to an implant or to an association loop (for example a suture or a thread) of the implant. In an embodiment, the slot 226 can be provided at the tip 208 of the insertion member 202. In accordance with some embodiments, the slot 226 is at least one selected from the group consisting of a T slot, an L slot, an angle shaped slot, and the like. The T slot can be configured to prevent the association loop from coming out of the slot 226 for example during bi-directional manipulation of the insertion member 202 during placement. In some embodiments, the insertion member 202 may be associated to a carrier or a dart or an anchor of the implant at the tip 208 of the insertion member 202.

In some embodiments, the channel of the insertion member 220 that is provided within the housing 218 can have various dimensions based on requirements and based on dimensions of the insertion member 202 that is configured to be disposed within the channel. In some embodiments, the width of the channel 220 is slightly more than the outer diameter of the insertion member 202. Further, in some other embodiments, the width of the channel 220 can be substantially greater than the diameter of the insertion member 202. In some embodiments, the height of the channel 220 is slightly more than the outer diameter of the insertion member 202. Further, in some other embodiments, the height of the channel 220 can be substantially greater than the diameter of the insertion member 202. The insertion member 202 can also have varying heights or diameters.

The medical device 200 further includes the adjustment member 204 as discussed above. The adjustment member 204 is configured to be coupled to the insertion member 202 distally and configured to be advanced and retracted, thereby advancing and retracting the insertion member 202 with respect to the housing 218 or the insert channel 220. The adjustment member 204 has a proximal end portion 228 and a distal end portion 230.

In some embodiments, the adjustment member 204 includes a hub 232 coupled to the distal end portion 212 of the insertion member 202 and configured to be advanced and retracted based on an application of an external force. The straight portion 216 of the insertion member 202 may terminate at the hub 232. The hub 232 has a proximal end portion 234 and a distal end portion 236.

In some other embodiments, the adjustment member 204 includes a hub 232 and a syringe 238. The hub 232 is similar to that described above and having a proximal end portion 234 and a distal end portion 236 similar to the hub 232 described above. The syringe 238 is configured to be coupled to the distal end 236 of the hub 232. In certain embodiments, the lumen of the insertion member 202 may be used to deliver medications such as anesthetics and the like through the syringe 238. In other embodiments the syringe 238 can also be used as a handle. In some embodiments a three ring syringe is used. In other embodiments, a two ring syringe or an O-ring and the like kinds of syringes may be used. In some embodiments, the syringe 238 may be connected to the hub 232 through a medical luer connection. In other embodiments, the syringe 238 may be connected to the hub 232 through other kinds of connections and coupling or fasteners. In some embodiments, the syringe 238 can be removably coupled to the hub 232. In other embodiments, the syringe 238 can be fixedly coupled to the hub 232 such that the hub 232 and the syringe 238 form an integral part of the adjustment member 204.

In some embodiments, the proximal end of the hub 234 is configured to be coupled to the insertion member 202 such that the insertion member 202 is configured to be advanced and/or retracted based on an application of an external force and/or release of the force exerted through the syringe 238. In other embodiments, the hub 234 can be advanced and/or retracted based on an application of an external force and/or release of the force exerted through the hub 232 directly, when the syringe 238 is not used.

Figure 2B:
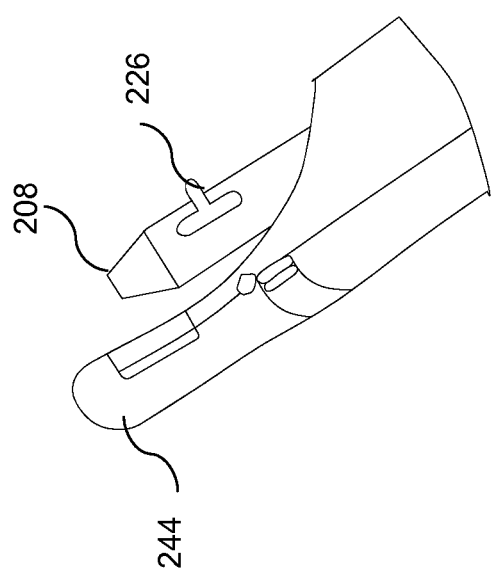
FIG. 2B illustrates an enlarged view of a portion of the medical device of FIG. 2A, in accordance with an embodiment of the present invention.
Figure 2C:
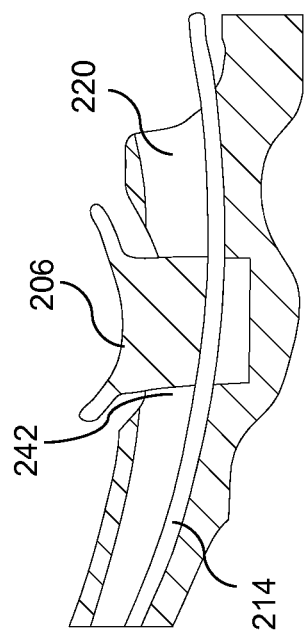
FIG. 2C illustrates an enlarged cross-sectional view of a portion of the medical device of FIG. 2A, in accordance with an embodiment of the present invention.
Figure 2D:
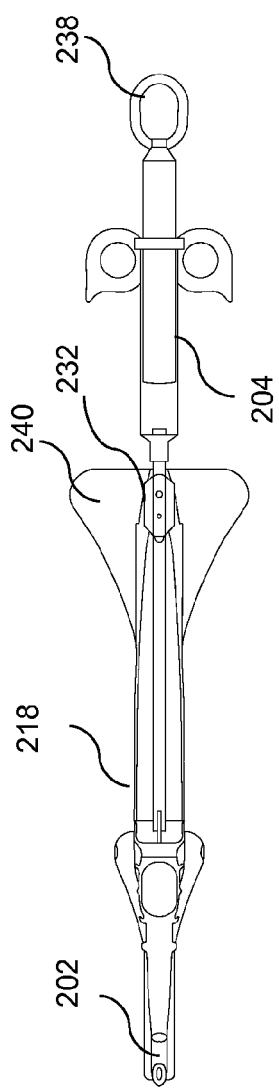
FIG. 2D illustrates a top view of a medical device configured to deliver a bodily implant in a patient's body, in accordance with an embodiment of the present invention.

In some embodiments, the adjustment member 204 can further include an orientation indicator 240 (shown in FIG. 2D). The orientation indicator 240 may be configured to indicate a degree of orientation of the insertion member tip 208 while the insertion member 202 advances into a bodily tissue. In some embodiments, the orientation indicator 240 includes wings or ears that are positioned along the distal portion 212 of the adjustment member 204 circumferentially. The orientation indicator 240 may provide a visual indication of the tip 208 orientation of the insertion member 202 such that it relates to row, yaw and pitch movements of the medical device 200. In some embodiments, the insertion member 202 is extended or advanced incrementally as the insertion member 202 is tracked and felt as it ascends and reaches the tissue layers, minimizing insertion member 202 deflection and maximizes needle stiffness relative to the extended length. The angle of the insertion member 202 introduction can be felt as well as seen by the orientation indicator 240.

As discussed above, the medical assembly 200 further includes the button 206. The button 206 can be moveably coupled to the housing 218 of the insertion member 202. In various embodiments, the button 206 may be coupled to the housing 218 of the insertion member 202 through various fasteners that provide the capability to the button 206 to move with respect to the housing 218. For example, in some embodiments, the button 206 may include projections on one or multiple sides such that these projections are configured to slide through one or multiple recesses provided in the housing 108.

The button 206 is configured to elevate away from a surface of the housing 218 as the insertion member 202 advances through the insertion member channel 220. The button 206 is further configured to be lowered toward the housing 218 by an application of force and contact the insertion member 202 so as to deflect and friction fit it within the insertion member channel 220 against inner surface of the channel 220. The button 206 is further configured to temporarily fix location of the insertion member 202 with respect to the housing 218 or the insertion member channel 220. The housing 218 may further include a button channel 242 such that the button 206 is configured to move inside the button channel 242 up and down. Further, the insertion member 202 when disposed inside the housing 218 is configured to extend through the button channel 242. In accordance with some embodiments, the button 106 is at least one selected from the group consisting of a lever, a trigger, and the like.

In accordance with various other embodiments, the button mechanism can include a cam, gear slide, ratchet, interference, friction-operated element, wedge, and the like to temporarily fix location of the insertion member 202 with respect to the housing 218 or the insertion member channel 220.

The insertion member channel 220 includes the curved portion 222 and the straight portion 224 as discussed above. In a completely advanced or extended position of the insertion member 202 with respect to the housing 218, the straight portion 216 of the insertion member 202 may be configured to fit into the curved portion 222 of the housing 218. In the advanced configuration, the button 206 may elevate away from the housing 218 because of a deflection in the insertion member 202 that pushes it upward. In a completely retracted position of the insertion member 202 with respect to the housing 218, the straight portion 216 of the insertion member 202 is configured to move out of the curved portion 222 of the housing 218. The retraction of the insertion member 202 may cause the button 206 to depress because the insertion member 102 gains or tries to gain its original shape that moves the button downward. In accordance with several embodiments, the movement of the button 206 up and down with respect to the insertion member channel 220 may be configured to temporarily fix location of the insertion member 202 with respect to the housing 218. For example, when the button 206 is in depressed state, it contacts the insertion member 202 to fix its location while the insertion member 202 is free to advance or retract when the button 206 is in elevated state.

FIGS. 2B and 2C illustrates enlarged views of portions of the medical device illustrated in FIG. 2A. FIG. 2B illustrates an enlarged view of the proximal end portion of the insertion member and the proximal end portion of the housing. As illustrated in FIG. 2B, in some embodiments, the insertion member 202 may have a slot 226 for association to an implant with the tip 208 at the proximal end 210 of the insertion member 202 as discussed above. In some embodiments, the tip 208 of the insertion member 202 is configured to be disposed within the housing 218 before insertion, as shown in FIG. 2B, such that bodily tissues are not damaged. FIG. 2C illustrates an enlarged cross-sectional view of the button 206 slid into the button channel 242 provided in the housing 218.

Figure 2E:
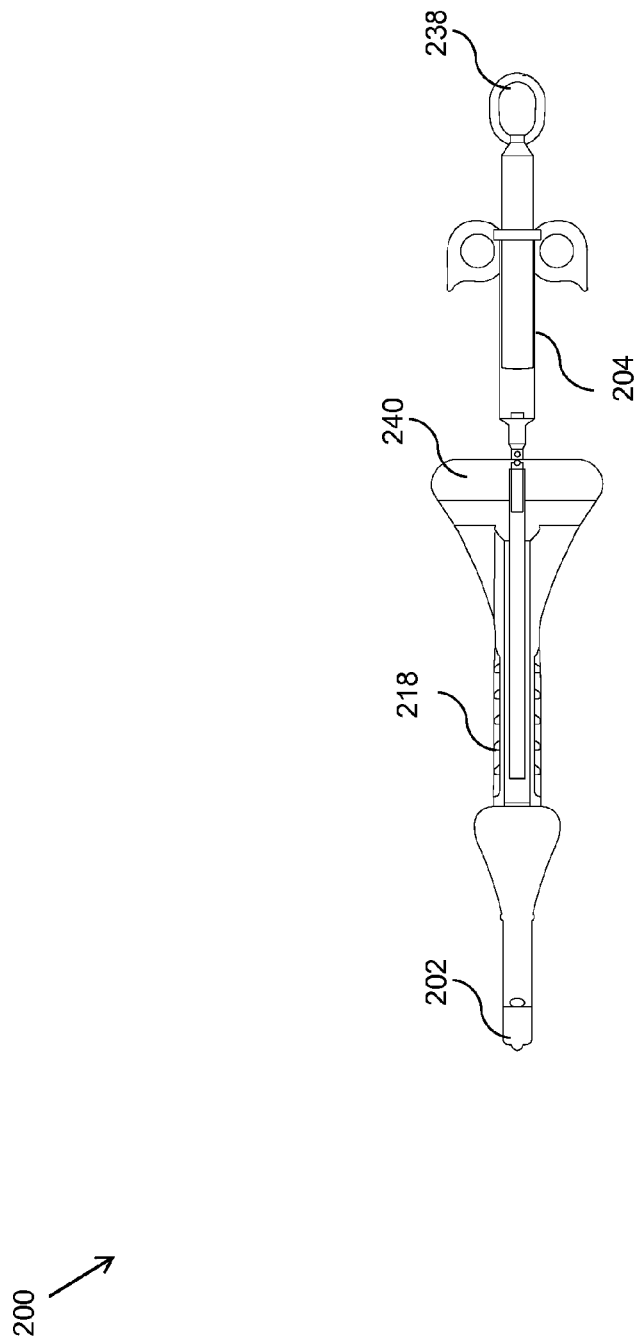
FIG. 2E illustrates a bottom view of a medical device configured to deliver a bodily implant in a patient's body, in accordance with an embodiment of the present invention.
Figure 3:
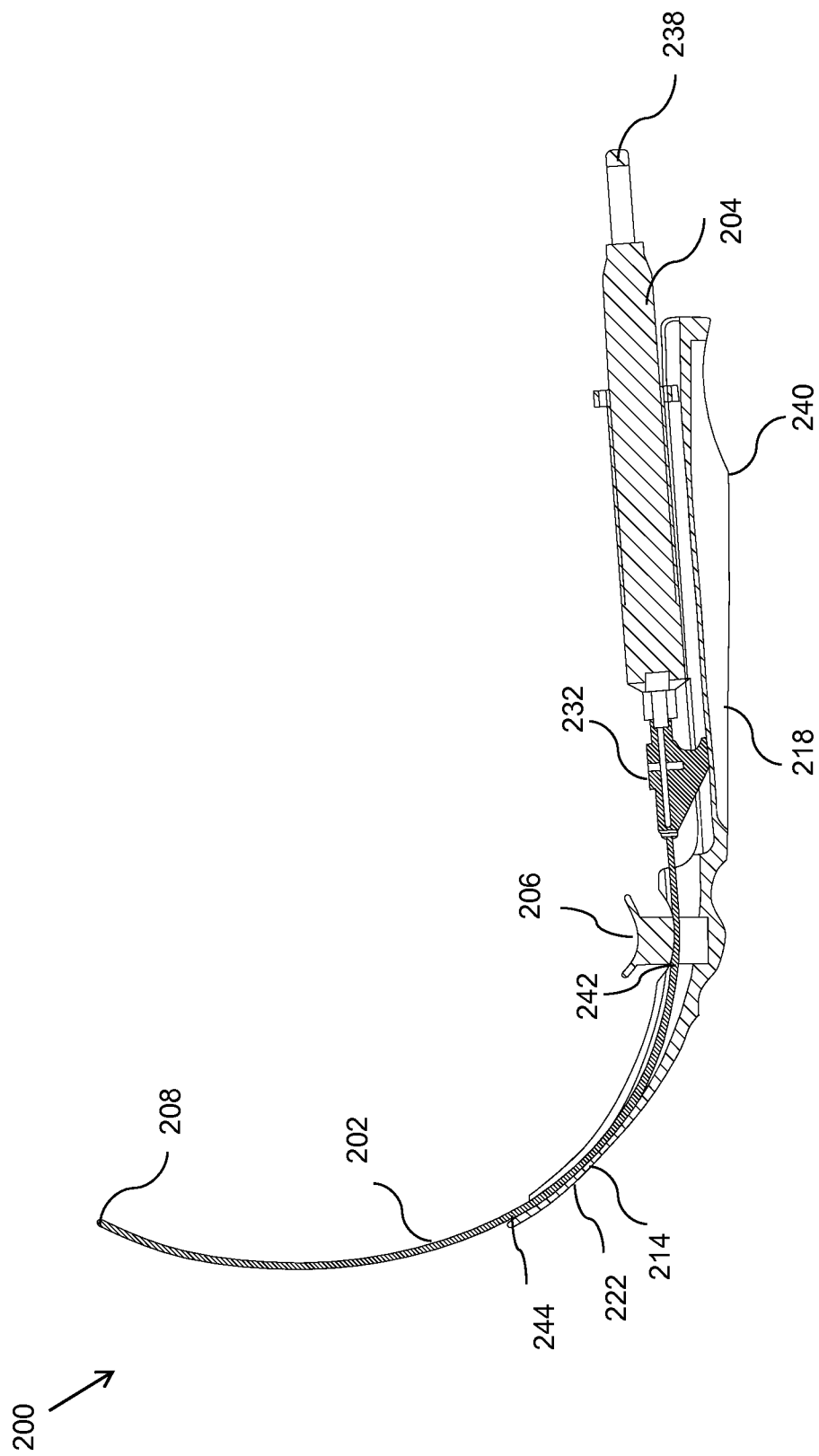
FIG. 3 is a side view a medical device in an advanced or extended configuration, in accordance with an embodiment of the present invention.

The different views of the medical device 200 taken along different angles are illustrated in FIGS. 2D-2E. FIG. 2D illustrates a top view of the medical device 200. FIG. 2E illustrates a bottom view of the medical device 200. FIGS. 2D-2E illustrates the completely retracted configuration of the insertion member 202 such that the complete insertion member channel 220 receives the insertion member 202 or a portion of the insertion member 202. This can also be referred to as a normal configuration. In this configuration, the curved portion 214 of the insertion member 202 rests in the curved portion 222 of the channel 220 and the straight portion 216 of the insertion member 202 rests in the straight portion 224 of the channel 220. In accordance with this configuration, the insertion member 202 is substantially free from any stress due to flexing, bending or deflection. In the completely retracted position, the straight portion 216 of the insertion member 202 may be configured to exit the curved portion 222 of the housing 218 upon recede through the adjustment member 204 and thereby configured to cause the button 206 to depress. As against to the completely retracted configuration, the insertion member 202 can be disposed within the housing 218 or the insertion member channel 220 such that the insertion member 202 is partially or completely advanced. The advanced or extended configuration is illustrated in FIG. 3. This can be done by advancing the insertion member with respect to the housing 218 or the insertion member channel 220. The adjustment member 204 is configured to adjust the location of the insertion member 202 with respect to the housing 218 such that upon advancement, the insertion member 202 has moved with respect to the housing 218. As the insertion member 202 is advanced or extended, the straight portion 218 of the insertion member 202 may fit into the curved portion 224 of the housing 220 upon advancement through the adjustment member 204 and thereby cause the button 206 to elevate and thereby extend or advance the inserting member 202 outward from the housing 218.

In some embodiments, the insertion member may be flexible. In accordance with these embodiments, the shape of the insertion member 202 may change as the insertion member 202 is extended or retracted from the housing 218. Since the straight portion 214 of the insertion member 202 enters the curved portion 222 of the channel 220, therefore the straight portion 214 of the insertion member 202 gets deflected because of the channel curvature. This causes the insertion member 202 to be spring loaded. Also, the deflected straight portion 214 will tend to straighten itself out. In this case, the insertion member 202 bows toward the small curvature of the channel 220 and elevate the button 206. The elevated button 206 can be pressed downward that further deflects the straight portion 214 of the insertion member 202. This produces a tighter insertion member curvature along the straight portion 214 causing the insertion member 202 to bind in the insertion member channel 220 and the button channel 242. In accordance with these embodiments, the curvatures of the insertion member 202 may not be similar to the curvatures of the insertion member channel 220. However, since the insertion member 202 is flexible, it can assume the shape of the channel 220 when disposed therein.

The support 246 (such as fulcrum) of the medical device 200 and the housing may remain unchanged and free from any shape change. In the advanced configuration, the portions of the insertion member 202 that extend from a tip 224 of the housing 218 may be subjected to deflection. In order to minimize deflection and maximize control insertion member 202 placement, the insertion member 202 is extended from the housing 218 in incremental lengths to maximize the stiffness of the insertion member 202 relative to its extended length, while the fulcrum 246 remains unchanged.

The insertion member 202 may have varying heights. In some embodiments, the height of the insertion member channel 220 may be much greater than the diameter of insertion member 202. In other embodiments, the height of the insertion member channel 220 may be slightly greater than the diameter of insertion member 202. In certain other embodiments, the height of the insertion member channel 220 is greater than the height of the insertion member 202 exiting the hub.

Figure 4A:
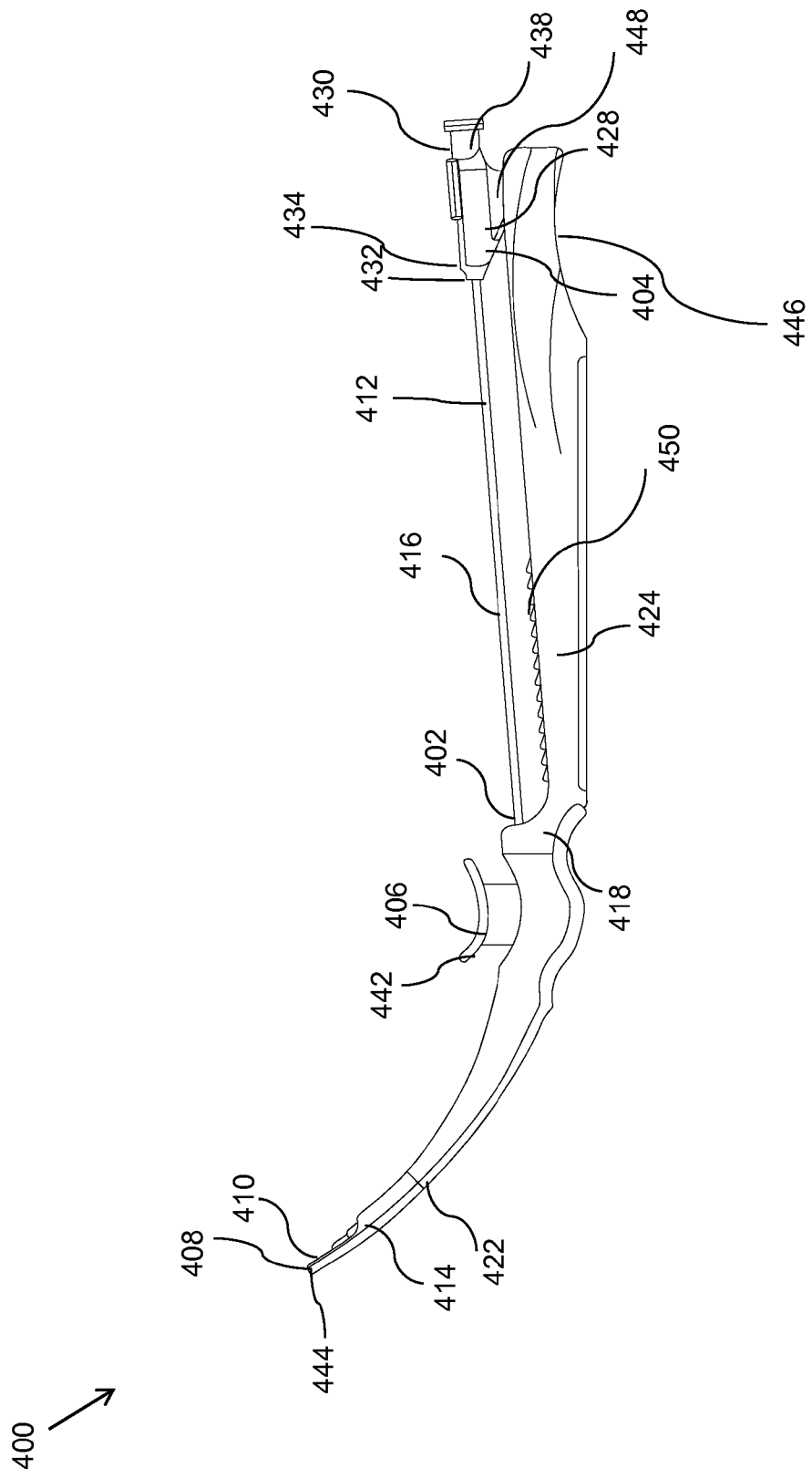
FIG. 4A illustrates a side view of a medical device configured to deliver a bodily implant in a patient's body, in accordance with an embodiment of the present invention.

FIG. 4A illustrates a perspective side view of a medical device 400, in accordance with an embodiment of the present invention. The medical device 400 includes an insertion member 402, an adjustment member 404, and a button 406.

The insertion member 402 includes a tip 408 and is configured to be inserted into a tissue layer and/or puncture bodily tissues. In some embodiments the tip 408 may be blunt. In other embodiments the tip 408 may be sharp. In certain embodiments the tip 408 may be conical in shape. In other embodiments the tip 408 may have any other shape. The insertion member 402 has a proximal end portion 410 and a distal end portion 412.

The insertion member 402 can have a variety of shapes and sizes depending on the surgical requirements. In certain embodiments, the insertion member 402 can be a surgical needle configured to pierce through a patient's body during insertion. The surgical needle may be made of a metal such as stainless steel.

The insertion member 402 has a curved portion 414 proximate the tip 408 of the insertion member 402 and a straight portion 416 distally located from the tip 408 of the insertion member 402. The insertion member 402 is configured to be disposed within an insertion member housing 418. The insertion member housing 418 may hereafter be referred to as housing 418 merely for the purpose of simplicity of the description without limiting the scope of the invention. The housing 418 includes a channel or a passageway 420 such that a portion of the insertion member 402 or the complete insertion member 402 is configured to move within the insertion member channel 420. The insertion member channel 420 includes a curved portion 422 and a straight portion 424. In some embodiments, the curved channel portion 422 and straight channel portion 424 are designed with curvatures that are substantially similar to the curvatures of the curved portion 414 and straight portion 416 of the insertion member 402. For example, the curvature of the curved portion 422 of the insertion member channel 420 can be similar to the curvature of the curved portion 414 of the insertion member 402 such that upon disposing the insertion member 402 within the channel 420, the curved portion 414 of the insertion member 402 can easily sit into the curved portion 422 of the channel 420 without being deflected or stressed due to flexing, bending or deflection. Similarly, the curvature of the straight portion 424 of the channel 420 can be similar to the curvature of the straight portion 416 of the insertion member 402 such that the straight portion 416 of the insertion member 402 can easily sit into the straight portion 424 of the channel 420 without being deflected or stressed due to flexing, bending or deflection. Therefore, the complete insertion member 402 is configured to be disposed and sit inside the channel 420 without being stressed due to the bending or deflection in at least one of the configurations. The configurations may be defined as a location of the insertion member 402 with respect to the housing 418 or the insertion member channel 420. There can be innumerable configurations based on the various locations of the insertion member 402 with respect to the housing 418 or the insertion member channel 420.

In some embodiments, the insertion member 402 can include a lumen that extends from the proximal end portion to the distal end portion of the insertion member 402. In some embodiments, the insertion member 402 has a small outer diameter to minimize injury to patients. For example, in some embodiments, the outer diameter may be 0.062 inches. In other embodiments, the dimensions of the outer diameters may be different.

Figure 5:
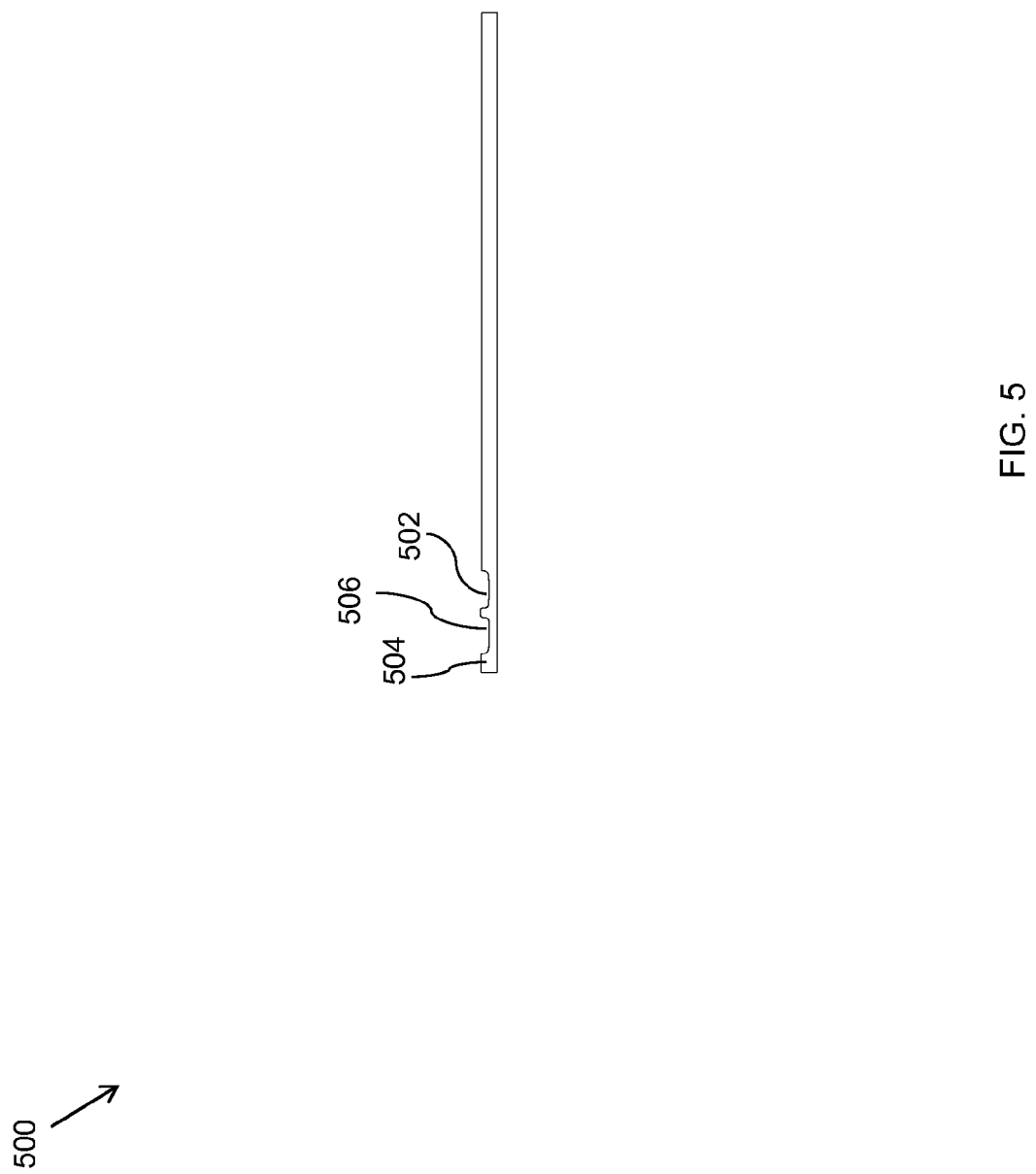
FIG. 5 illustrates a dilator, in accordance with an embodiment of the present invention.

As illustrated in FIG. 4B, in some embodiments, the tip 408 of the insertion member 402 has a stepped design such that the diameter or width of the tip varies for certain portions in the stepped design to form different steps kinds of structures. The stepped design is further provided with a retention bump 426. The stepped design of the tip 408 along with the retention bump 426 is used for association of the insertion member 402 with the implant or to an association loop (for example a suture or a thread) of the implant. In some embodiments, the stepped design of the tip 408 can be used to associate it with a dilator such as the dilator 500 as shown in FIG. 5. The dilator 500 may be configured to assist in delivery of bodily implants and medical devices inside the body by widening a passageway there through. The dilator 500 can include a slot 502 near dilator tip 504 such that the retention bump 426 is configured to associate and get fixed into the slot 502 of the dilator 500. The bump 426 is configured to prevent dislodging of the dilator 500 or the implant during delivery or implantation. A second slot 506 may also be provided in the dilator 500 that provides a clearance to allow an instrument or a device such as a hemostat to reach between the dilator 500 and insertion member 402 that is coupled to the dilator 500 and therefore assists in removal of the dilator 500 from the insertion member tip.

The medical device 400 further includes the adjustment member 404 as discussed above. The adjustment member 404 is configured to be coupled to the insertion member 402 distally and configured to be advanced and retracted, thereby advancing and retracting the insertion member 402 with respect to the housing 418 or the insert channel 420. The adjustment member 404 has a proximal end portion 428 and a distal end portion 430.

In some embodiments, the adjustment member 404 includes a hub 432 coupled to the distal end portion 412 of the insertion member 402 and configured to be advanced and retracted based on an application of an external force. The straight portion 416 of the insertion member 402 may terminate at the hub 432. The hub 432 has a proximal end portion 434 and a distal end portion.

In some other embodiments, the adjustment member 404 includes a hub 432 and a syringe 438. The hub 432 is similar to that described above and having a proximal end portion 434 and a distal end portion similar to the hub 132 described above. The syringe 438 is configured to be coupled to the distal end of the hub 432. In certain embodiments, the lumen of the insertion member 402 may be used to deliver medications such as anesthetics and the like through the syringe 438. In other embodiments the syringe 438 can also be used as a handle. In some embodiments a three ring syringe is used. In other embodiments, a two ring syringe or an O-ring and the like kinds of syringes may be used. In some embodiments, the syringe 438 may be connected to the hub 432 through a medical luer connection. In other embodiments, the syringe 438 may be connected to the hub 432 through other kinds of connections and coupling or fasteners. In some embodiments, the syringe 438 can be removably coupled to the hub 432. In other embodiments, the syringe 438 can be fixedly coupled to the hub 432 such that the hub 432 and the syringe 438 form an integral part of the adjustment member 204.

In some embodiments, the proximal end of the hub 434 is configured to be coupled to the insertion member 402 such that the insertion member 402 is configured to be advanced and/or retracted based on an application of an external force and/or release of the force exerted through the syringe 438. In other embodiments, the hub 434 can be advanced and/or retracted based on an application of an external force and/or release of the force exerted through the hub 432 directly, when the syringe 438 is not used.

Figure 4C:
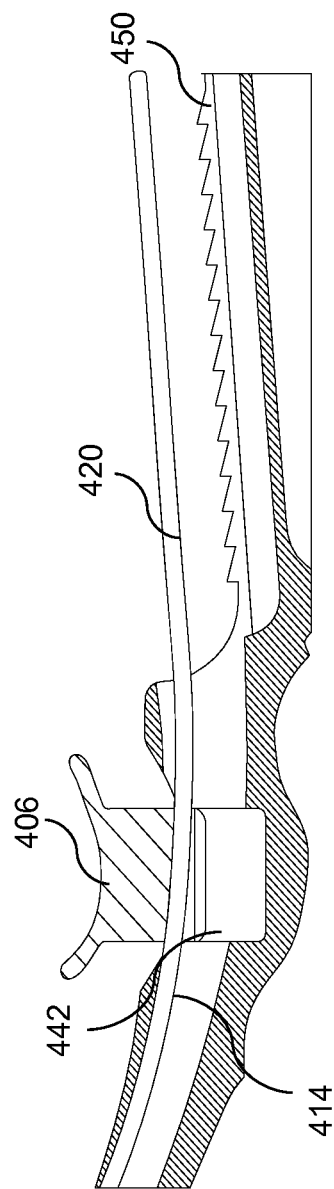
FIG. 4C illustrates an enlarged view of a portion of the medical device of FIG. 4A, in accordance with an embodiment of the present invention.
Figure 4D:
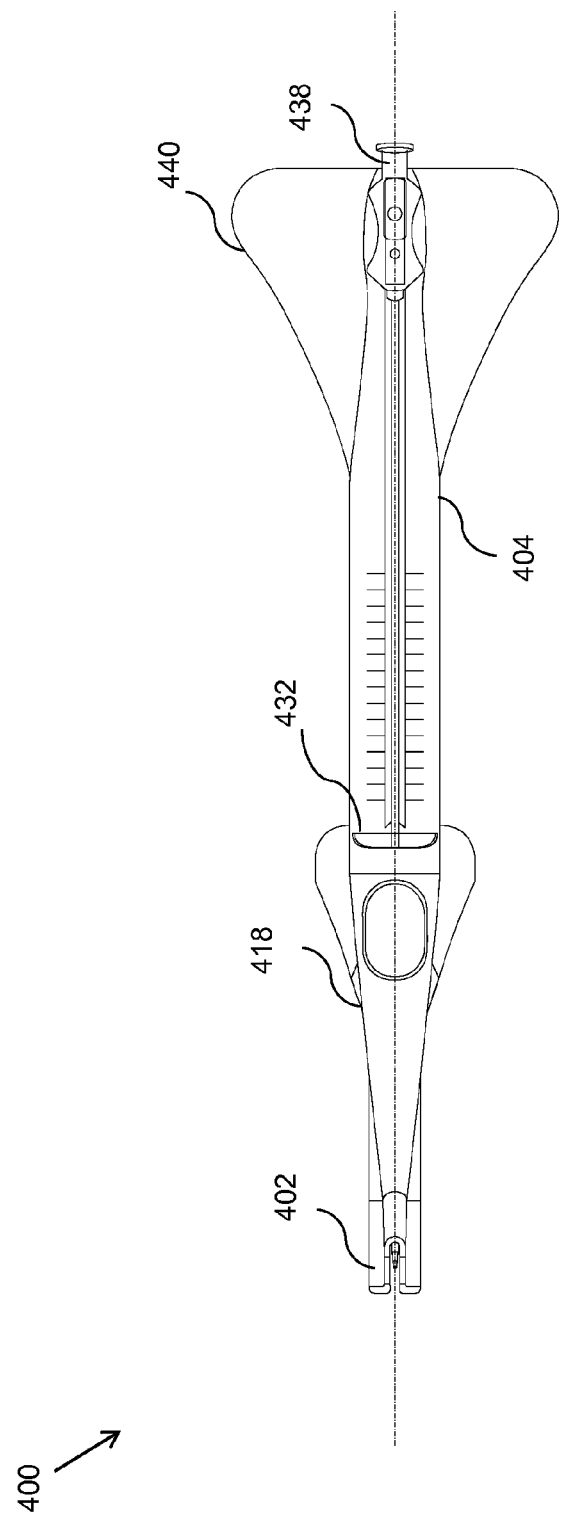
FIG. 4D illustrates a top view of a medical device configured to deliver a bodily implant in a patient's body, in accordance with an embodiment of the present invention.

In some embodiments, the adjustment member 404 can further include an orientation indicator 440 (shown in FIG. 4D). The orientation indicator 440 may be configured to indicate a degree of orientation of the insertion member tip 408 while the insertion member 402 advances into a bodily tissue. In some embodiments, the orientation indicator 440 includes wings or ears that are positioned along the distal portion 412 of the adjustment member 404 circumferentially.

As discussed above, the medical assembly 400 further includes the button 406. The button 406 can be moveably coupled to the housing 418 of the insertion member 402. In various embodiments, the button 406 may be coupled to the housing 418 of the insertion member 402 through various fasteners that provide the capability to the button 406 to move with respect to the housing 418. For example, in some embodiments, the button 406 may include projections on one or multiple sides such that these projections are configured to slide through one or multiple recesses provided in the housing 418.

The button 406 is configured to elevate away from a surface of the housing 418 as the insertion member 402 advances through the insertion member channel 420. The button 406 is further configured to be lowered toward the housing 418 by an application of force and contact the insertion member 402 so as to deflect and friction fit it within the insertion member channel 420 against inner surface of the channel 420. The button 406 is further configured to temporarily fix location of the insertion member 402 with respect to the housing 218 or the insertion member channel 420. The housing 418 may further include a button channel 442 such that the button 406 is configured to move inside the button channel 442 up and down. Further, the insertion member 402 when disposed inside the housing 418 is configured to extend through the button channel 442. In accordance with some embodiments, the button 406 is at least one selected from the group consisting of a lever, a trigger, and the like.

The insertion member channel 420 includes the curved portion 422 and the straight portion 424 as discussed above. In a completely advanced or extended position of the insertion member 402 with respect to the housing 418, the straight portion 416 of the insertion member 402 may be configured to fit into the curved portion 422 of the housing 418. In the advanced configuration, the button 406 may elevate away from the housing 418 because of a deflection in the insertion member 402 that pushes it upward. In a completely retracted position of the insertion member 402 with respect to the housing 418, the straight portion 416 of the insertion member 402 is configured to move out of the curved portion 422 of the housing 418. The retraction of the insertion member 402 may cause the button 406 to depress because the insertion member 402 gains or tries to gain its original shape that moves the button downward. In accordance with several embodiments, the movement of the button 406 up and down with respect to the insertion member channel 420 may be configured to temporarily fix location of the insertion member 402 with respect to the housing 418. For example, when the button 406 is in depressed state, it contacts the insertion member 402 and fix its location while the insertion member 402 is free to advance or retract when the button 406 is in elevated state.

In some embodiments, the adjustment member 404 may further include a hook 448 and the insertion member 402 may include a stop mechanism 450 such that the hook 448 is configured to engage the stop mechanism 450 to prevent the insertion member 402 from retracting. However, when the button 406 is released, the button 406 and the hub are elevated by a spring (not shown) provided in the insertion member 402 and the hook 448 disengages from the stop mechanism 450. And then the insertion member 402 can be retracted. In accordance with various embodiments, the stop mechanism 450 can be a teethed section having a set of teeth and the hook 448 can have a slot or a bent section such that the teethed section can engage the slot or the bent section of the hook 448. In accordance with other embodiments, there can be various other types of stop mechanisms and hooks.

FIGS. 4B and 4C illustrates enlarged views of portions of the medical device illustrated in FIG. 4A. FIG. 4B illustrates an enlarged view of the proximal end portion of the insertion member and the proximal end portion of the housing. FIG. 4C illustrates an enlarged cross-sectional view of the button 406 slid into the button channel 442 provided in the housing 418.

Figure 4E:
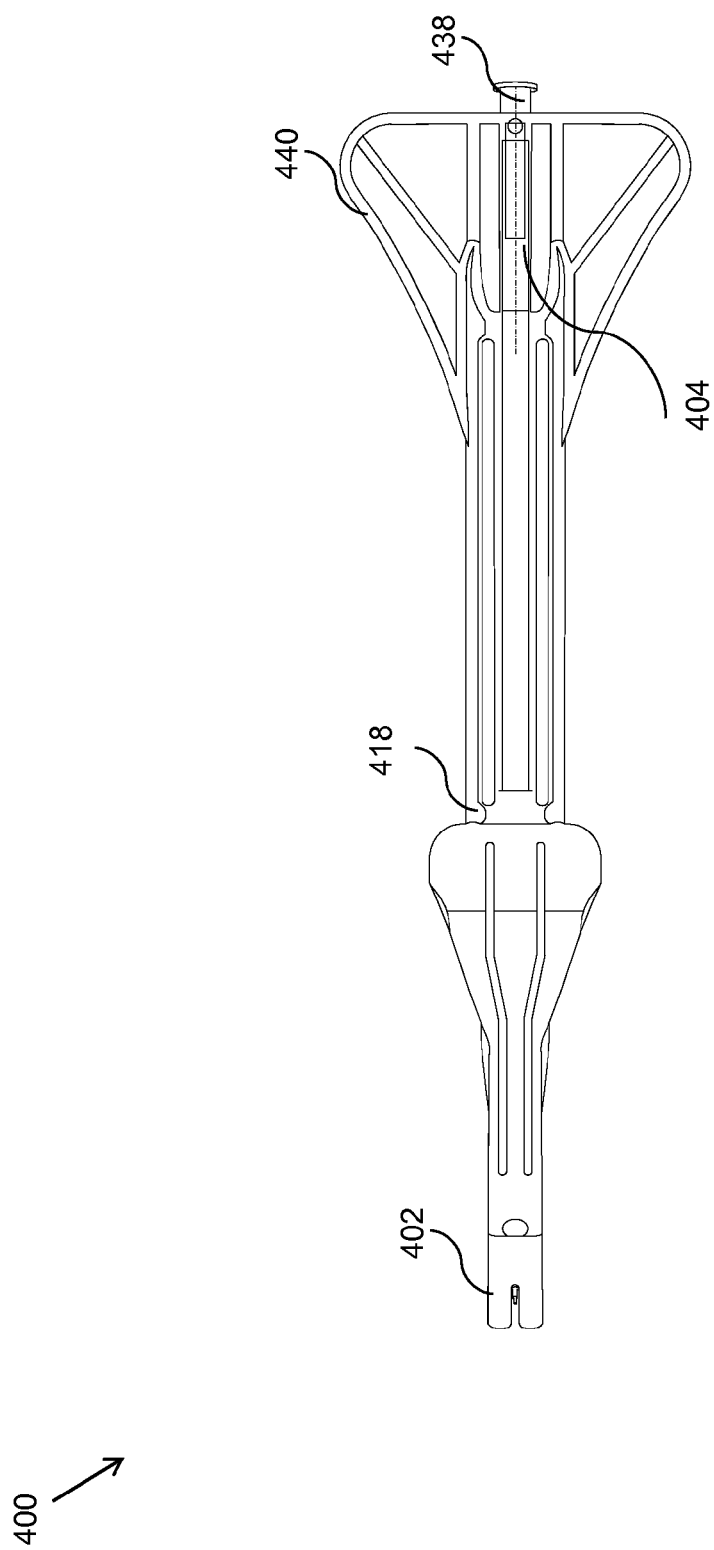
FIG. 4E illustrates a bottom view of a medical device configured to deliver a bodily implant in a patient's body, in accordance with an embodiment of the present invention.

The different views of the medical device 400 taken along different angles are illustrated in FIGS. 4D-4E. FIG. 4D illustrates a top view of the medical device 400. FIG. 4E illustrates a bottom view of the medical device 400.

In some embodiments, the insertion member may be flexible. In accordance with these embodiments, the shape of the insertion member 402 may change as the insertion member 402 is extended or retracted from the housing 418. Since the straight portion 414 of the insertion member 402 enters the curved portion 422 of the channel 420, therefore the straight portion 414 of the insertion member 402 gets deflected because of the channel curvature. This causes the insertion member 402 to be spring loaded. Also, the deflected straight portion 414 will tend to straighten itself out. In this case, the insertion member 402 bows toward the small curvature of the channel 420 and elevate the button 406. The elevated button 406 can be pressed downward that further deflects the straight portion 414 of the insertion member 402. This produces a tighter insertion member curvature along the straight portion 414 causing the insertion member 402 to bind in the insertion member channel 420 and the button channel 442. In accordance with these embodiments, the curvatures of the insertion member 402 may not be similar to the curvatures of the insertion member channel 420. However, since the insertion member 402 is flexible, it can assume the shape of the channel 420 when disposed therein.

Figure 6A:
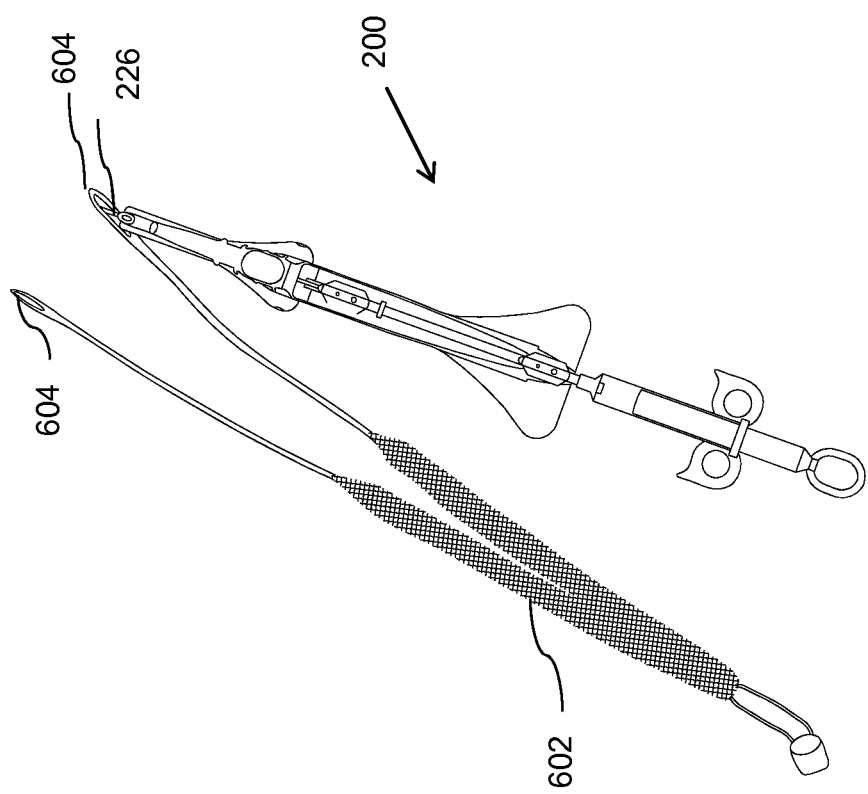
FIG. 6A illustrates an association of an implant with the medical device, in accordance with an embodiment of the present invention.

FIG. 6A illustrates an association of an implant 602 with the medical device 200 as discussed above. As illustrated, FIG. 6A shows one side of the implant 602 with an association loop 604 that may be associated to the insertion member 202 of the medical device 200. In accordance with various embodiments, the insertion member of the medical device 200 can include the slot 226 configured to receive a portion of the loop 604 such that the medical device 200 can be associated with the loop 604 through the slot 226. In some embodiments, the loop 604 can be a thread or a suture. The various types of slots are discussed above in conjunction with FIG. 1. An enlarged perspective view of the association of the implant 602 with the medical device 200 is illustrated in FIG. 6B.

In accordance with the embodiments presented above, various types of implants can be employed. In some embodiments, the implant 602 is made of a synthetic material such as polymeric material and the like. In some embodiments, the implant 602 includes a polymeric mesh body. In other embodiments, the implant 602 includes a polymeric planar body without mesh cells and structures. Exemplary polymeric materials are polypropylene, polyester, polyethylene, nylon, PVC, polystyrene, and the like. In some embodiments, the implant 602 is made of a non-woven polymeric material. In some embodiments, the surface of the implant 602 is smooth to avoid or reduce irritation on adjacent body tissues during medical interactions. Additionally, in some embodiments, the implant 602 is stretchable and flexible to adapt movements along the anatomy of the human body and reduce suture pullout. In some other embodiments, the implant 602 can be made of natural materials such as biologic material or a cadaveric tissue and the like.

FIGS. 7A-7E illustrate a method of use of a medical device for placement of an implant 602 in a patient's body opening, in accordance with an embodiment of the present invention. The medical assembly 200 is being used hereafter to describe the placement procedure. However, other medical assemblies as described in conjunction with various figures mentioned above can also be employed in a similar manner. Various body portions such as vagina 702, urethra 704, bladder 706, uterus 708, rectum 710, pubic bone 712, fingers of an operator 714, right hand 716, left hand 718, rectus fascia 720, pubic symphysis 722 are also depicted in conjunction with FIGS. 7A-7E.

Figure 8A:
FIGS. 8A-8B illustrate the implant placed inside the patient's body, in accordance with an embodiment of the present invention.
Figure 8B:
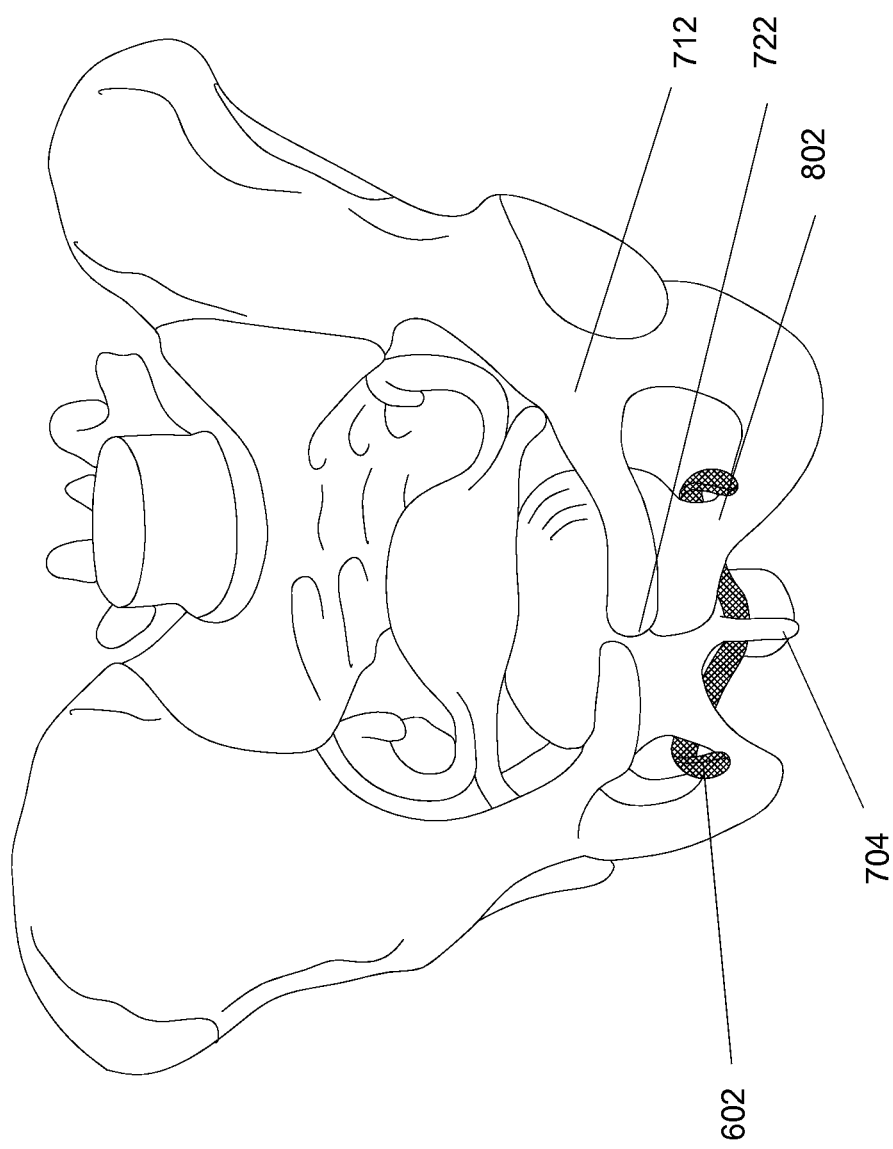

FIGS. 8A-8B illustrate the implant placed inside the patient's body. FIG. 8A illustrates positioning of the medical assembly 200 inside a female body through a retropubic approach. The retropubic approach allows positioning the implant 602 under the urethra 704 in a U shape manner. The ends of the implant 602 are brought up behind the pubic bone 712 and out through incisions above the pubic bone 712, and coupled to tissues adjacent to the pubic bone 712.

In some other embodiments, the method can be achieved through a transobturator approach as shown in FIG. 8B. In accordance with this approach, the implant 602 is passed under the urethra 704 and out through incisions in the groin 802 compartment of the thigh (not shown in the diagram).

Figure 9:
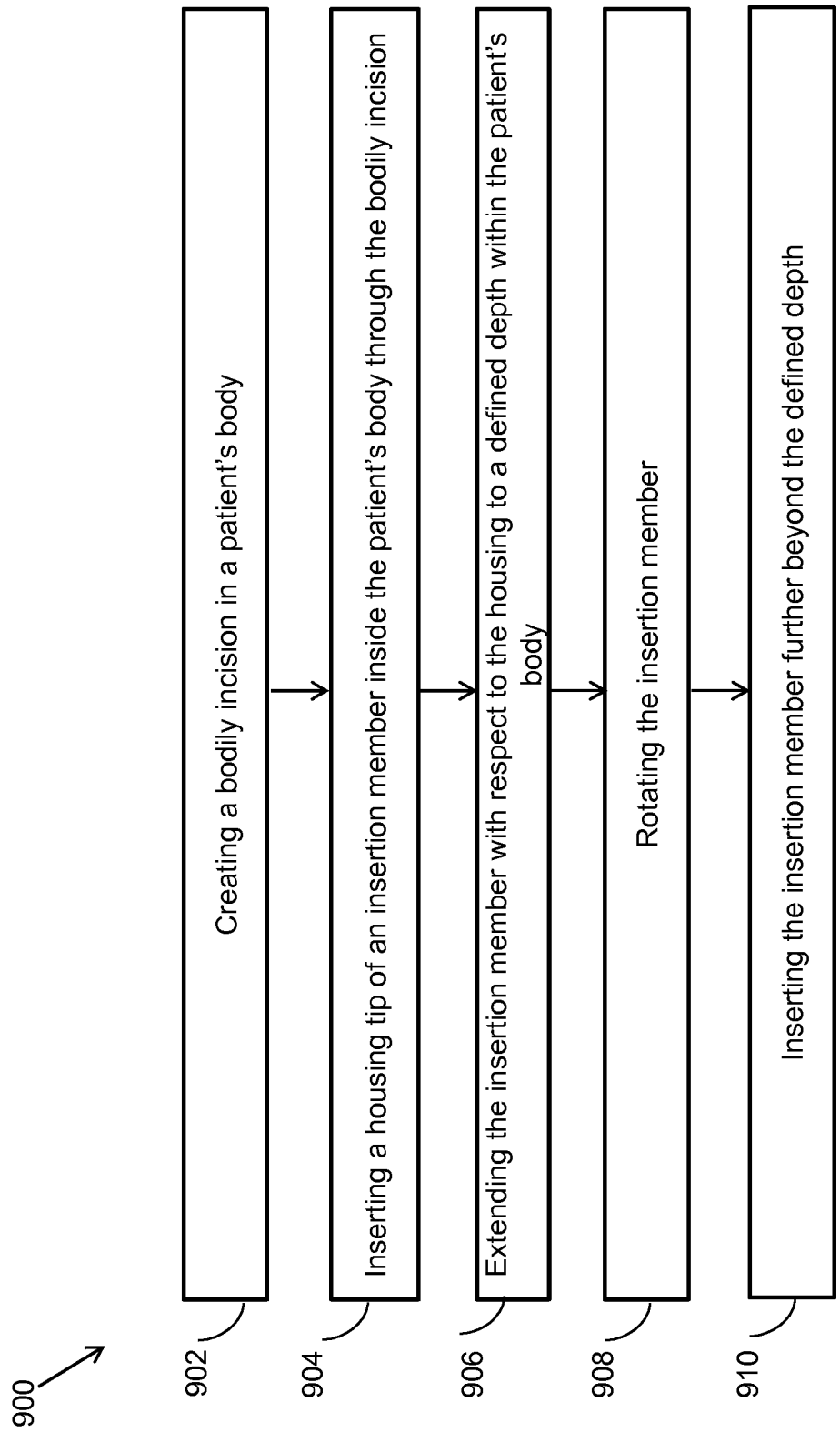
FIG. 9 illustrates a flowchart depicting a method for treatment of a pelvic floor disorder in a patient's body in accordance with an embodiment of the present invention.

FIG. 9 illustrates a flowchart depicting a method 900 for treatment of a pelvic floor disorder in a patient's body in accordance with an embodiment of the present invention. The present invention allows treatment of a pelvic floor disorder using a medical device such as the medical device 200. The medical device 200 is hereafter used to describe the placement in an exemplary embodiment. However, it must be appreciated that other medical devices such as the medical devices mentioned above may also be placed in the similar manner.

The medical device 200 includes the insertion member 202, adjustment member 204, and the button 206 as described in conjunction with FIG. 2. Referring now to FIGS. 7A-7E, FIGS. 8A-8B, and FIG. 9, a method for treatment of the pelvic floor disorder in a patient's body is described using the medical device 200 of FIG. 2.

The method 900 includes creating a bodily incision in the patient's body for inserting the medical device 200 at step 902. The method of creating the incision and the location of the incision can vary based on the approach used.

Figure 7A:
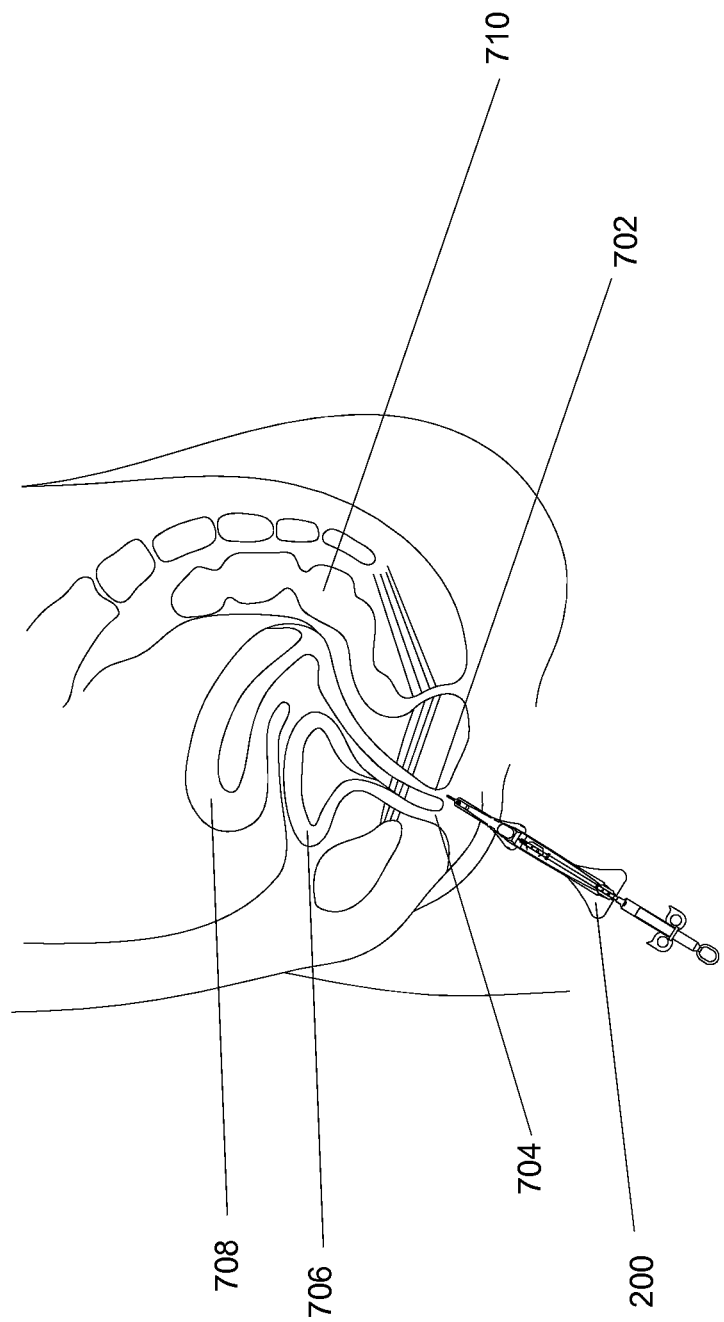

The method further includes inserting the housing tip 244 of the insertion member 202 inside the patient's body through the bodily incision at step 904 as illustrated in FIG. 7A. In some embodiments, an operator may direct the housing tip toward the pubic bone 702 before insertion. Therefore, upon insertion, the insertion member moves toward the pubic bone rather than other bodily organs that are not required to be dissected or punctured and their puncturing may cause injury to the patient such as the bladder, urethra, bowel, and the like. In this manner, an inadvertent puncture of these bodily organs is avoided.

The housing tip 232 is inserted while the insertion member 202 is fully retracted with respect to the housing 218. In the fully retracted configuration of the insertion member 202 with respect to the housing 218, the tip of the insertion member completely stays inside the housing 218 such that there is no danger of damage to the bodily tissues due to sharp tip.

Once the housing tip 244 is inserted, the insertion member 202 is extended or advanced with respect to the housing 218 to a defined depth within the patient's body at step 906 such that the tip 208 of the insertion member 202 comes in contact with the pubic bone 712 upon advancement to the defined depth. The defined depth is controlled and adjusted by the adjustment member 206. For example, the operator can advance and control advancement of the insertion member with respect to the housing with the use of the hub by hand or with the use of the syringe connected to the hub. In some embodiments, the method may also include passing or injecting a medication through the syringe 238 during advancement or after advancement of the insertion member 202 into the patient's body.

In some embodiments, the operator can stop advancement of the insertion member 202 when the insertion member tip 208 contacts the pubic bone 712. The contact with the pubic bone 712 is illustrated in FIG. 7D. The contact of the insertion member 202 with the pubic bone 712 can be felt based on a tactile feedback at an operator's or surgeon's hand. The advancement can be stopped from the hub or the syringe of the adjustment member 206 right when the contact is felt so that any damage to the pubic bone 712 may also be avoided. In order to ensure better and safe surgery, the operator may advance the insertion member 202 incrementally so that the contact is felt as soon as it happens. Further, based on surgical experiences and patient's anatomical tests and pre-surgery reports, the operator can also know in advance when the insertion member tip 208 is about to contact the pubic bone 712. In this case, the operator may slow down the speed of advancement of the insertion member 202 with respect to the housing. Similarly, in order to feel contact with the pubic bone 712 at the right time, various other measures can be taken by the operator. Nevertheless, a contact with the pubic bone 712 is less harmful and less damaging as compared to a contact with the delicate body organs like bladder or urethra. Therefore, a proper and a directed orientation toward the pubic bone 712 rather than any other location may avoid severe injuries to these body organs such as unwanted dissection.

As soon as the contact with the pubic bone 712 is felt, the insertion member 202 is rotated along an X-X axis that extends orthogonally through the page containing the figure at step 908. The dot marked as X-X represents the axis that is orthogonal to the page. The rotation is shown by arrow A in FIG. 7E. The insertion member 202 is now able to be further advanced past or above the pubic bone 712 as illustrated in FIG. 7E. The rotation can be done by the operator by tilting the housing 218 clockwise or anticlockwise when the operator senses a contact with the pubic bone 712 based on tactile feedback. The insertion member 202 is then advanced or extended further with respect to the housing 218 past the pubic bone 712 and beyond the defined depth at step 910.

After more advancement, there is a possibility that the insertion member tip 208 again comes in contact with the pubic bone 712. Therefore, the advancement is stopped and then the insertion member tip 208 is again rotated a degree or two to further advance the insertion member 202. This process of advancing the insertion member 202 past the pubic bone 712 and then rotating it when it contacts the pubic bone 712 is repeated till the insertion member tip 208 reaches rectus fascia 720 or pubic symphysis 722 or any other target location.

Once the insertion member tip 208 reaches rectus fascia 720 or pubic symphysis 722 as illustrated in FIG. 7E, the fascia may tent due to the force exerted by the insertion member tip 208.

In some embodiments, the method 900 may further include pushing the button 206 downward and holding the button 206 with thumb in order to maintain and prevent the insertion member 202 of the medical device 200, from retracting and advancing. In the advanced or retracted position, the portions of the insertion member 202 that extend from a tip 224 of the housing 218 may be subjected to deflection. In order to minimize deflection and maximize control, the insertion member 202 is extended from the housing 218 in incremental lengths to maximize the stiffness of the insertion member 202 relative to its extended length. The button 206 may fix the insertion member 202 with respect to the housing 218 temporarily. The button 206 may also prevent deflection of the insertion member 202 and keep it stiff. The button 206 is further configured to be lowered toward the housing 218 by an application of force and contact the insertion member 202 so as to deflect and tighten it within the insertion member channel 220. The button 206 is further configured to temporarily fix location of the insertion member 202 with respect to the housing 218 or the insertion member channel 220.

Figure 7B:
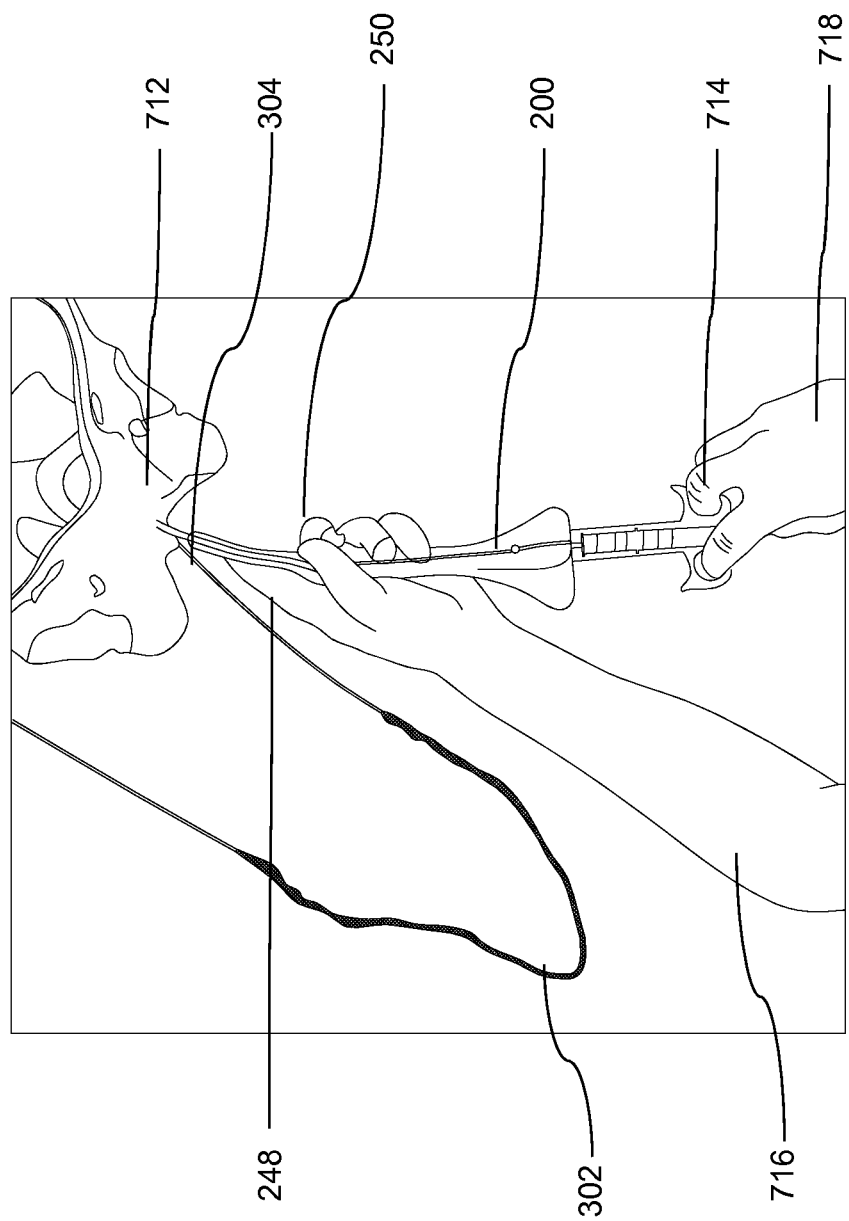
Figure 7D:
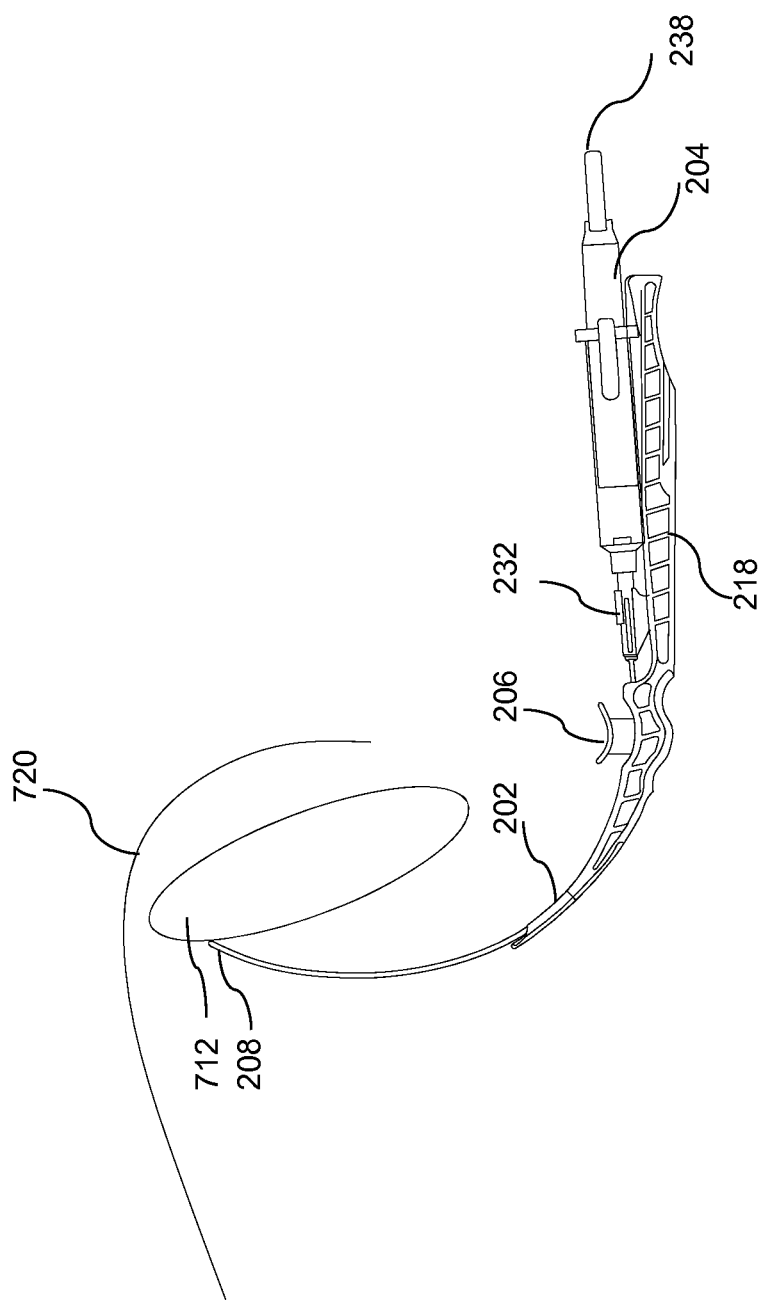
Figure 7E:
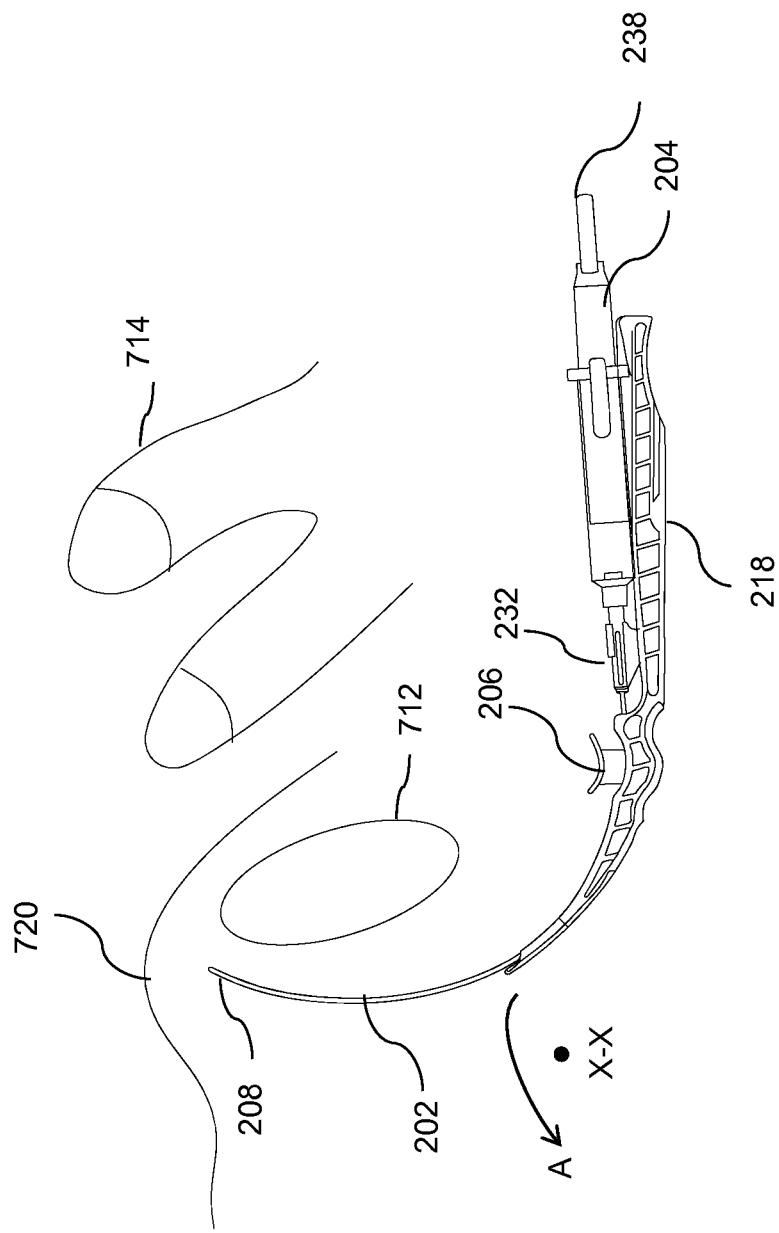

FIG. 7B illustrates one way of holding the medical device 200. Variations can occur among operators or surgeons. In some embodiments, the operator or surgeon may use his/her left hand 716 to support and aim the medical device 200 for placement of the implant 602 in the patient's body opening, in accordance with an embodiment of the present invention. In some embodiments, the housing 218 of the insertion member 202 may be provided with an index finger and mid finger rest. The flatness of the finger rest may aid the operator or surgeon to direct the tip of the medical device 200 toward an indent target. The operator or surgeon may operate the button 206 with his/her thumb. The operator or surgeon may further use his/her right hand 718 for tactile feedback and to advance or retract the syringe connected to hub 238 while aspirating and injecting. The medical device 200 is symmetrical and can be used in a similar manner if the hands are switched. The fingers 714 of the operator attached to the three ring syringe may be configured to form a V-shape, as illustrated in FIG. 7E. This may result in pressing against the fascia above the insertion member tip 208 to allow the insertion member tip 208 to puncture through the fascia.

In accordance with some embodiments, a user can grip the insertion member housing, the insertion member 102, and the adjustment member 106 by hand to prevent the insertion member from retracting while the second hand can be used to depress an abdominal wall of the patient.

Finally, the hand is removed from the syringe 238. Further, the association loop 604 of the implant 602 can be removed from the insertion member tip 208 and the insertion member 202 can be retracted and removed.

The incision can finally be closed using a suture or any other technique after the medical device is removed from the patient's body.

In some embodiments, a medical device includes an insertion member, an adjustment member, and a button (or an actuator or actuation mechanism). The insertion member includes a tip. The insertion member has a curved portion proximate the tip of the insertion member and a straight portion distally located from the tip. The curved and straight portions of the insertion member are configured to be placed into a channel within a housing. The adjustment member is coupled to the insertion member distally and configured to be advanced and refracted, thereby advancing and retracting the insertion member with respect to the housing. The button is moveably coupled to the housing of the insertion member. The button is configured to elevate away from a surface of the housing as the insertion member advances with respect to the housing and is configured to be lowered toward the housing by an application of force and contact the insertion member so as to deflect and friction fit the insertion member within the channel. The button is further configured to temporarily fix location of the insertion member with respect to the housing.

In some embodiments, the housing includes a button channel such that the button is configured to move inside the button channel up and down with respect to the insertion member channel. In some embodiments, the insertion member, when disposed inside the housing is configured to be threaded or extend through the button channel. In some embodiments, the insertion member channel includes a curved portion and a straight portion. In some embodiments, the straight portion of the insertion member is configured to enter the curved portion of the insertion member channel and thereby configured to cause the button to elevate. In some embodiments, the straight portion of the insertion member is configured to retract and move from the curved portion toward the straight portion of the insertion member channel and is thereby configured to cause the button to depress during retraction.

In some embodiments, the adjustment member includes a hub coupled to a distal end portion of the insertion member and configured to be advanced and retracted based on an application of an external force. In some embodiments, the adjustment member includes a hub and a syringe configured to be coupled to a distal end of the hub. A proximal end of the hub is configured to be coupled to the insertion member such that the insertion member is configured to be advanced or retracted based on an application of an external force or release of the force exerted on the syringe. In some embodiments, the syringe is further configured to inject a medication into a patient's body.

In some embodiments, the device includes an orientation indicator provided on the adjustment member. The orientation indicator is configured to indicate a degree of orientation of the insertion member tip while the insertion member advances into a bodily tissue.

In some embodiments, the tip of the insertion member includes a slot configured to engage an association loop of an implant. In some embodiments, the implant is configured to support bodily tissues for the treatment of a pelvic floor disorder.

In some embodiments, a method for treatment of a pelvic floor disorder in a patient's body includes creating a bodily incision in the patient's body; inserting a housing tip of an insertion member inside the patient's body through the bodily incision, the insertion member including a curved portion and a straight portion, wherein the curved and straight portions are configured to be placed into a channel within the housing of the insertion member, wherein the housing tip is inserted while the insertion member is fully retracted with respect to the housing; extending the insertion member with respect to the housing to a defined depth within the patient's body such that a tip of the insertion member comes in contact with a pubic bone; rotating the insertion member such that the insertion member is able to be further advanced past the pubic bone; and inserting the insertion member further beyond the defined depth.

In some embodiments, the method includes directing the housing tip toward the pubic bone before insertion such that an inadvertent puncture of bodily organs is avoided. In some embodiments, the method includes puncturing target tissues upon inserting the insertion member to a desired depth within the patient's body past the pubic bone. In some embodiments, the method includes feeling a contact of the insertion member with the pubic bone based on a tactile feedback at an operator's hand. In some embodiments, the method includes pressing a button provided on the housing, the button configured to tighten and deflect the insertion member within the housing, the button further configured to temporarily fix location of the insertion member with respect to the housing.

In some embodiments, the insertion member is coupled to a syringe and the method includes injecting a medication through the syringe during advancement of the insertion member into the patient's body.

In some embodiments, the method includes repeating the step of extending the insertion member with respect to the housing followed by rotating the insertion member until a contact with the pubic bone is felt. In some embodiments, the method includes closing the bodily incision.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device comprising:
   an insertion member with a tip, the insertion member having a curved portion proximate the tip of the insertion member and a straight portion distally located from the tip;
   a housing configured to house at least a portion of the insertion member, the housing defining an insertion member channel, wherein the curved and straight portions of the insertion member are configured to be placed into the insertion member channel within the housing of the insertion member, the insertion member channel including a curved portion;
   an adjustment member coupled to the insertion member distally and configured to be advanced and retracted, thereby advancing and retracting the insertion member with respect to the housing; and
   a button moveably coupled to a portion of the housing having the curved portion of the insertion member channel, the button configured to elevate away from a surface of the housing as the insertion member advances with respect to the housing and configured to be lowered toward the housing by an application of force and contact the insertion member so as to deflect and friction fit the insertion member within the insertion member channel, wherein the button is further configured to temporarily fix location of the insertion member with respect to the housing,
   wherein the straight portion of the insertion member is configured to retract and move from the curved portion of the insertion member channel toward a straight portion of the insertion member channel.

2. The medical device of claim 1, wherein the housing includes a button channel such that the button is configured to move inside the button channel up and down with respect to the insertion member channel.

3. The medical device of claim 2, wherein the insertion member when disposed inside the housing is configured to be threaded through the button channel.

4. The medical device of claim 1, wherein the straight portion of the insertion member is configured to enter the curved portion of the insertion member channel and thereby configured to cause the button to elevate.

5. The medical device of claim 1, wherein the button is configured to depress during retraction of the straight portion of the insertion member from the curved portion of the insertion member channel toward the straight portion of the insertion member channel.

6. The medical device of claim 1, wherein the adjustment member includes a hub coupled to an end portion of the insertion member and configured to be advanced and retracted based on an application of an external force.

7. The medical device of claim 1, wherein the adjustment member includes a hub and a syringe configured to be coupled to a first end of the hub, wherein a second end of the hub is configured to be coupled to the insertion member such that the insertion member is configured to be advanced or retracted based on an application of an external force or release of the force exerted on the syringe.

8. The medical device of claim 7, wherein the syringe is further configured to inject a medication into a patient's body.

9. The medical device of claim 1 further including:
   an orientation indicator provided on the adjustment member, the orientation indicator configured to indicate a degree of orientation of the insertion member tip while the insertion member advances into a bodily tissue.

10. The medical device of claim 1, wherein the tip of the insertion member includes a slot configured to engage an association loop of an implant.

11. The medical device of claim 10, wherein the implant is configured to support bodily tissues for treatment of a pelvic floor disorder.

12. A medical device comprising:
an insertion member with a tip;
a housing configured to house at least a portion of the insertion member, the housing defining an insertion member channel;
an adjustment member coupled to the insertion member and configured to be advanced and refracted, thereby advancing and retracting the insertion member with respect to the housing; and
a button moveably coupled to a portion of the housing, wherein the button, when pressed towards an inside of the housing, is configured to extend into the insertion member channel and contact the insertion member such that insertion member is pressed against an inner surface of the insertion member channel,
wherein a straight portion of the insertion member is configured to retract and move from a curved portion of the insertion member channel toward a straight portion of the insertion member channel.

13. The medical device of claim 12, wherein the button is further configured to temporarily fix a location of the insertion member with respect to the housing.

14. The medical device of claim 12, wherein the button defines a button channel, and the insertion member, when disposed inside the housing, is configured to extend through the button channel.

15. The medical device of claim 12, wherein the button is configured to elevate way from the inside of the housing such that the insertion member can move with respect to the housing.

16. The medical device of claim 12, wherein a shape of the insertion member changes as the insertion member extends or retracts from the housing.

17. The medical device of claim 12, wherein the button is configured to depress during retraction of the straight portion of the insertion member from the curved portion of the insertion member channel toward the straight portion of the insertion member channel.

* * * * *